US012637647B2

(12) United States Patent
Takata et al.

(10) Patent No.: US 12,637,647 B2
(45) Date of Patent: May 26, 2026

(54) MICROORGANISM CULTURE KIT

(71) Applicant: Murata Manufacturing Co., Ltd., Nagaokakyo (JP)

(72) Inventors: Masachika Takata, Nagaokakyo (JP); Hirofumi Sunahara, Nagaokakyo (JP); Yoshiteru Aoi, Higashihiroshima (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 1146 days.

(21) Appl. No.: 17/481,693

(22) Filed: Sep. 22, 2021

(65) Prior Publication Data

US 2022/0002649 A1     Jan. 6, 2022

Related U.S. Application Data

(63) Continuation of application No. PCT/JP2020/009166, filed on Mar. 4, 2020.

(30) Foreign Application Priority Data

Mar. 26, 2019     (JP) ................................. 2019-057730

(51) Int. Cl.
*C12M 1/00*          (2006.01)
*C12M 1/12*          (2006.01)
(Continued)

(52) U.S. Cl.
CPC ............ *C12M 23/44* (2013.01); *C12M 23/06* (2013.01); *C12M 23/34* (2013.01); *C12M 29/00* (2013.01)

(58) Field of Classification Search
CPC ...... C12M 23/06; C12M 23/34; C12M 23/44; C12M 23/46; C12M 29/00; C12M 29/10; C12M 41/00; C12P 17/16
See application file for complete search history.

(56) References Cited

U.S. PATENT DOCUMENTS

| | | | |
|---|---|---|---|
| 7,011,957 B2 | 3/2006 | Lewis et al. | |
| 2004/0132175 A1* | 7/2004 | Vetillard ................ | C12M 35/08 |
| | | | 435/297.1 |
| 2011/0236932 A1* | 9/2011 | Stobbe ................... | C12M 23/42 |
| | | | 435/71.1 |

FOREIGN PATENT DOCUMENTS

| | | |
|---|---|---|
| JP | 2009207394 A | 9/2009 |
| JP | 2009273399 A | 11/2009 |

(Continued)

OTHER PUBLICATIONS

International Search Report issued in PCT/JP2020/009166, dated Jun. 2, 2020.

(Continued)

*Primary Examiner* — Lydia Edwards
(74) *Attorney, Agent, or Firm* — ArentFox Schiff LLP

(57)          ABSTRACT

Devices and methods for culturing microorganisms are disclosed. In some aspects, the devices include two frame bodies. The two frame bodies may comprise a first-type frame body and a second-type frame body. The first-type frame body may comprise a first frame body surrounding a first internal space. The first frame body may comprise an inflow passage for a fluid to flow into the first internal space and an outflow passage for the fluid to flow out from the first internal space, the inflow passage and the outflow passage being each provided to be openable and closable. The second-type frame body may comprise a second frame body surrounding a second internal space. In some aspects, the two frame bodies are stackable on each other.

16 Claims, 18 Drawing Sheets

(51) Int. Cl.
_C12M 1/32_        (2006.01)
_C12M 3/00_        (2006.01)

(56)                References Cited

FOREIGN PATENT DOCUMENTS

| JP | 2010161979 A | 7/2010 |
| JP | 2012175973 A | 9/2012 |
| JP | 2016086654 A | 5/2016 |
| JP | 2019033678 A | 3/2019 |

OTHER PUBLICATIONS

Written Opinion of the International Search Report issued in PCT/JP2020/009166, dated Jun. 2, 2020.

\* cited by examiner

MICROORGANISM CULTURE KIT

CROSS-REFERENCE TO RELATED APPLICATIONS

The present application is a continuation of International Application No. PCT/JP2020/009166, filed Mar. 4, 2020, which claims priority to Japanese Patent Application No. 2019-057730, filed Mar. 26, 2019, the entire contents of each of which being incorporated herein by reference.

FIELD OF THE INVENTION

The present invention relates to a microorganism culture kit and related methods of culturing microorganisms using such devices.

BACKGROUND OF THE INVENTION

It has been said that only about 1% of microorganisms in the environment can be cultured by a conventionally performed agar-plate surface smear method. Such methods are limited due to several constraints. First, due to the closed culture environment, it is not possible to easily remove substances generated by the cultured microorganism. As a result, metabolites of the microorganism and environmental components accumulate in the culture and inhibit the growth and multiplication of the microorganism. Furthermore, it is difficult to maintain in a solid medium the concentration of a nutrient required for the growth of a target microorganism.

Prior researchers have attempted to addresses these concerns by performing the culturing while a liquid medium is continuously supplied, or by culturing microorganisms on a solid medium placed in a natural environment. Examples of such methods are described in Japanese Patent Application Pub. No. 2016-86654 and in U.S. Pat. No. 7,011,957, the entire contents of each of which being incorporated herein by reference. However, these methods are fail to provide an effective solution (e.g., due to the instability associated with attempts to culture microorganisms in a natural environment and limitations on the parameters that can be modified).

SUMMARY OF INVENTION

In some aspects, the present disclosure provides a microorganism culture kit that can be used to provide various culture conditions. These devices implement a simple design that can be rapidly configured, allowing researchers to study otherwise difficult to culture microorganisms. In some aspects, a microorganism culture kit according to the present invention includes: two frame bodies, in which the two frame bodies are each a first-type frame body or are the first-type frame body and a second-type frame body, in which the first-type frame body includes a first frame body surrounding a first internal space, the first frame body including an inflow passage for a fluid to flow into the first internal space and an outflow passage for the fluid to flow out from the first internal space, the inflow passage and the outflow passage being each provided to be openable and closable, in which the second-type frame body includes a second frame body surrounding a second internal space, and in which the two frame bodies are stackable on each other.

In some aspects, the first-type frame body is configured, in a state in which the inflow passage and the outflow passage are open, to circulate a nutrient-containing gas, a nutrient-containing liquid, an environmental component-containing gas, or an environmental component-containing liquid in the first internal space and able, in a state in which the inflow passage and the outflow passage are closed, to hold a microorganism-containing medium, a nutrient-containing material, or an environmental component-containing material in the first internal space, and wherein the second-type frame body is configured to hold a microorganism-containing medium, a nutrient-containing material, or an environmental component-containing material in the second internal space.

In some aspects, each of the two frame bodies has an annular shape and has an internal thread and an external thread, the two frame bodies being configured to be stacked on and coupled to each other as a result of the internal thread of one of the frame bodies being screwed with the external thread of the other of the frame bodies.

In some aspects, the two frame bodies are each a first-type frame body.

In some aspects, the two frame bodies are each a second-type frame body.

In some aspects, the first-type frame body includes a pipe extending outward from the inflow passage, wherein the pipe is configured to allow a fluid to be added to and flow into the inflow passage In some aspects, the microorganism culture kit comprises a cap body configured to close the first internal space and/or the second internal space of the frame bodies that are stacked on each other to cover the first internal space and/or the second internal space, and/or a base that supports the frame bodies that are stacked on each other In some aspects, the first-type frame body includes a pipe extending outward from the outflow passage, wherein the pipe is configured to allow a fluid to flow into the outflow passage.

In some aspects, the microorganism culture kit comprises a cap body configured to close the first internal space and the second internal space of the frame bodies that are stacked on each other to cover the first internal space and the second internal space.

In another general aspect, the disclosure provides methods of culturing a microorganism. For example, in some aspects, a method of culturing a microorganism, comprising: providing a microorganism-containing medium; and placing the microorganism-containing medium in any of the microorganism culture kits described herein. In some aspects, the microorganism-containing medium is placed in the first-type frame body or the second-type frame body of the microorganism culture kit. In some aspects, the microorganism-containing medium is placed in the first internal space of the first-type frame body or the second internal space of the first-type frame body.

DETAILED DESCRIPTION

Aspects of the present disclosure will be more specifically described below, with reference to the drawings where appropriate. However, it should be understood that while exemplary devices and methods are described, the present disclosure is not necessarily limited to those devices and methods alone.

Figure 1:
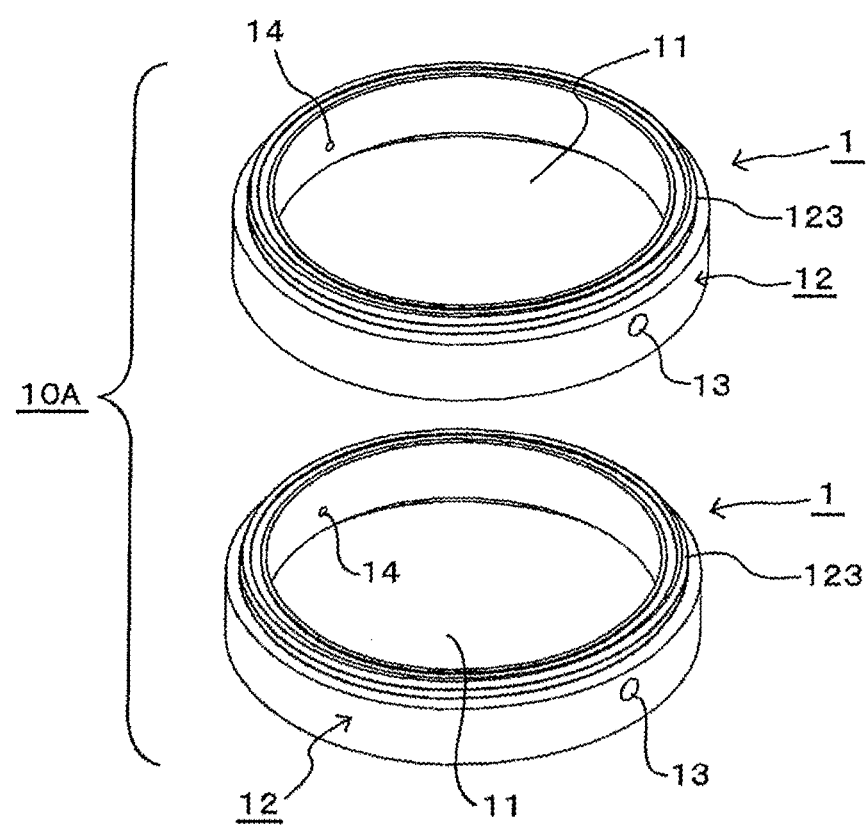
FIG. 1 is a perspective view illustrating a microorganism culture kit according to a first embodiment of the present invention.
Figure 2:
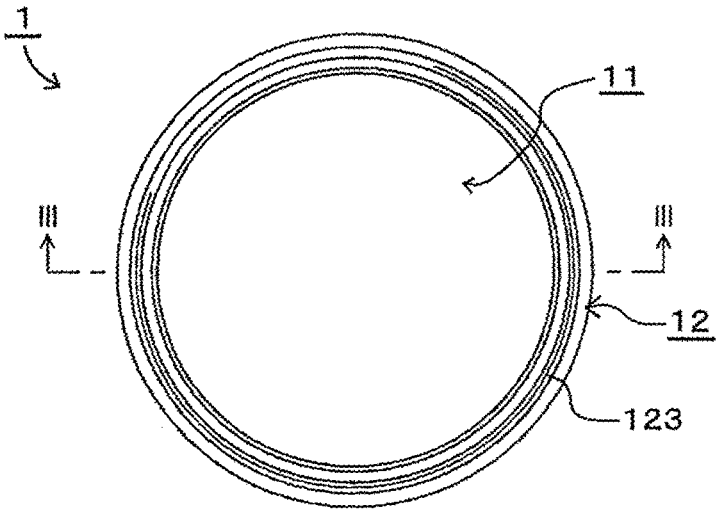
FIG. 2 is a plan view illustrating a first-type frame body of a microorganism culture kit.

In some aspects, a microorganism culture kit according to the present embodiment includes two frame bodies stackable on each other. As illustrated in FIG. 1, in a microorganism culture kit 10A according to the present embodiment, the two frame bodies may each be a first-type frame body 1. FIG. 2 is a plan view of the first-type frame body 1.

Figure 3:
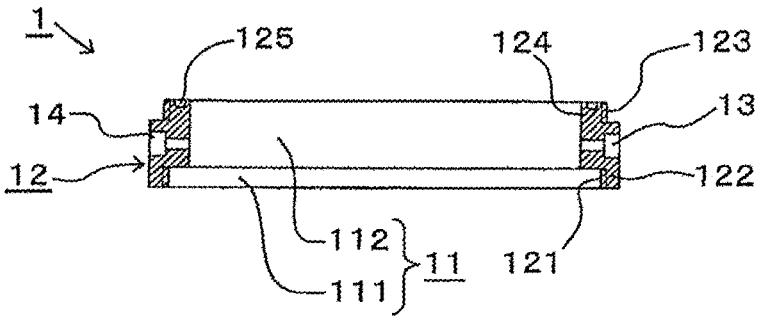
FIG. 3 is a sectional view along line in FIG. 2.

FIG. 3 is a sectional view along line III-III in FIG. 2. The first-type frame body 1 may include an annular first frame body 12 surrounding a first internal space 11. As illustrated in FIG. 3, the first frame body 12 may include, at a lower portion thereof, an annular external fitting portion 122 having an internal thread 121 and includes, at an upper portion thereof, an annular internal fitting portion 124 having an external thread 123. The external fitting portion 122 may have dimensions that enable external fitting to the internal fitting portion 124. The internal fitting portion 124 may have dimensions that enable internal fitting to the external fitting portion 122. The first internal space 11 may include an internal space 111 surrounded by the external fitting portion 122 and an internal space 112 other than the internal space 111. The internal fitting portion 124 may include an O-ring 125 at the upper surface thereof.

Figure 4:
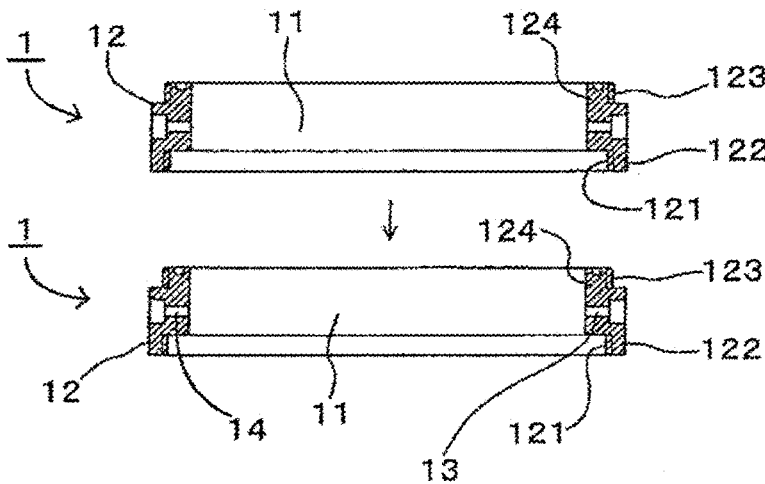
FIG. 4 is a sectional view illustrating work of coupling first-type frame bodies to each other.

As illustrated in FIG. 4, the two first-type frame bodies 1 may be configured to be stacked on and coupled to each other as a result of the internal thread 121 of the first-type frame body 1 positioned at an upper location being screwed with the external thread 123 of the first-type frame body 1 positioned at a lower location. The coupled two first-type frame bodies 1 are sealed by the O-ring 125 in this exemplary embodiment.

Figure 5:
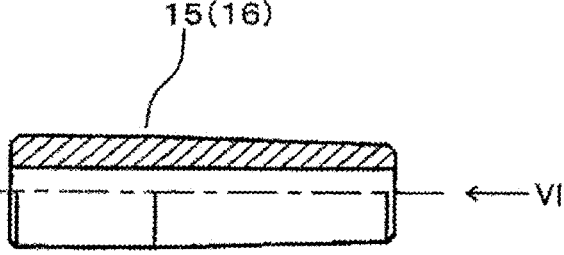
FIG. 5 is a partial sectional side view illustrating a vibrator.
Figure 6:
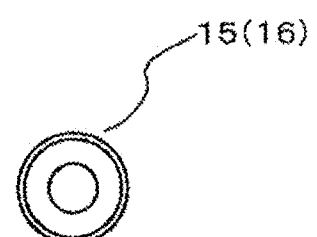
FIG. 6 is a view on arrow VI in FIG. 5.

Further, the first frame body 12 may an inflow passage 13 for a fluid to flow into the internal space 11 and an outflow passage 14 for the fluid to flow out from the internal space 11. In some aspects, it is preferable that a pipe 15 and/or a pipe 16, such as those illustrated in FIG. 5, be coupled to the inflow passage 13 and the outflow passage 14, respectively, and project radially toward the outside. FIG. 5 is a partial sectional side view of the pipe 15, and FIG. 6 is a view on arrow VI in FIG. 5. The inflow passage 13 and the outflow passage 14 are each closable by a plug 17 (refer to FIG. 7), instead of the pipe 15 and the pipe 16, being stuffed therein. Consequently, the inflow passage 13 and outflow passage 14 are openable and closable.

In a state in which the inflow passage 13 and the outflow passage 14 are open, the first-type frame body 1 is capable of circulating a fluid in the first internal space 11. The fluid is a nutrient-containing gas, a nutrient-containing liquid, an environmental component-containing gas, or an environmental component-containing liquid. In a state in which the inflow passage 13 and the outflow passage 14 are closed, the first-type frame body 1 is capable of holding, in the first internal space 11, a microorganism-containing medium, a nutrient-containing material, or an environmental component-containing material.

Figure 7:
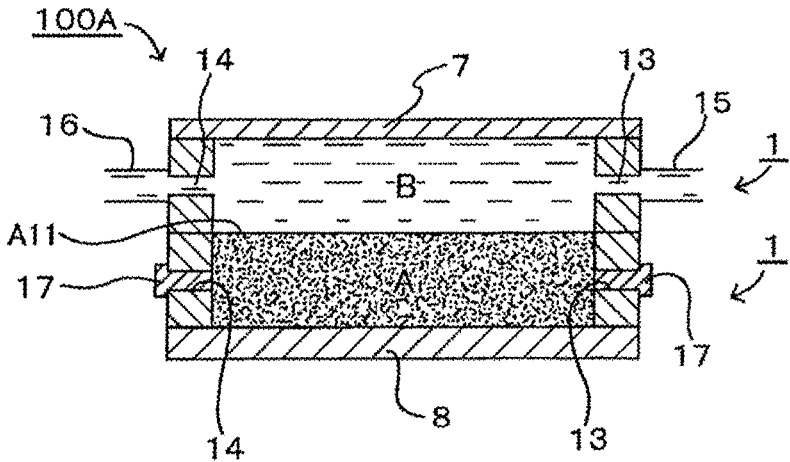
FIG. 7 is a schematic sectional view illustrating a microorganism culture apparatus constituted by the microorganism culture kit according to the first embodiment.

The microorganism culture kit 10A according to the present embodiment may be used as follows. As illustrated in FIG. 7, a two-layer stack structure body can be constructed by two first-type frame bodies 1 being stacked on each other, and the two-layer stack structure is usable as the microorganism culture apparatus 100A. In the two-layer stack structure body, the first-type frame body 1 in a state in which the inflow passage 13 and the outflow passage 14 are closed is disposed at a lower layer, and the first-type frame body 1 in a state in which the inflow passage 13 and the outflow passage 14 are open is disposed at an upper layer. In some aspects, preferably, a membrane filter (not illustrated) is disposed between the first-type frame body 1 at the upper layer and the first-type frame body 1 at the lower layer. The microorganism culture apparatus 100A may be configured such that the first-type frame body 1 at the lower layer holds a microorganism-containing medium in the first internal space 11 and the first-type frame body 1 at the upper layer circulates a nutrient-containing liquid in the first internal space 11. That is, the microorganism culture apparatus 100A may have a two-layer stack structure formed by a layer-like culture portion A formed by the first-type frame body 1 that is at the lower layer and that holds the microorganism-containing medium, and a layer-like nutrient supply portion B formed by the first-type frame body 1 that is at the upper layer and that is disposed at a first surface A11 of the culture portion A, the nutrient supply portion B supplying a nutrient to the culture portion A.

Figure 8:
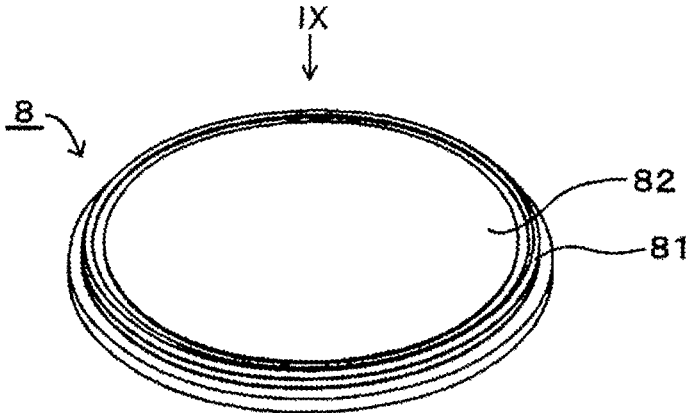
FIG. 8 is a perspective view of a base.
Figure 9:
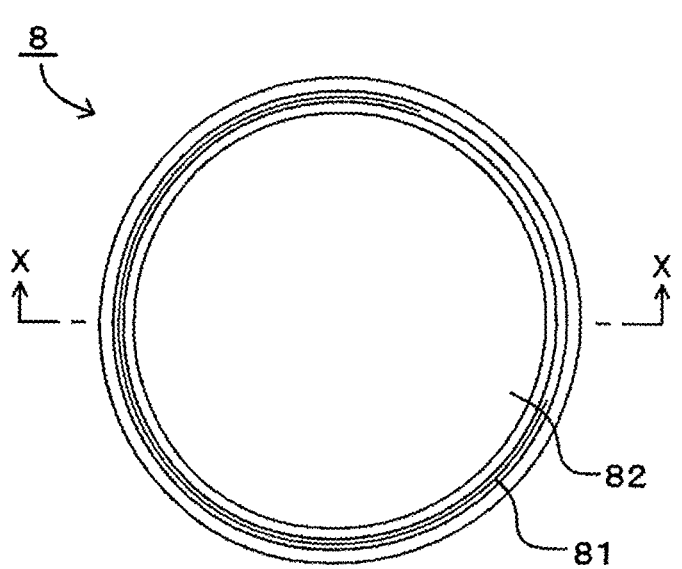
FIG. 9 is a view on arrow IX in FIG. 8.
Figure 10:
FIG. 10 is a sectional view along line X-X in FIG. 9.

In some aspects, preferably, the first-type frame body 1 at the lower layer is stacked on a base 8. The base 8 is illustrated in FIG. 8 to FIG. 10. FIG. 8 is a perspective view of the base 8. FIG. 9 is a view on arrow IX in FIG. 8. FIG. 10 is a sectional view along line X-X in FIG. 9. The base 8 is a circular plate body in plan view and includes, at an upper portion thereof, an internal fitting portion 82 having an external thread 81. The internal fitting portion 82 has dimensions that enable internal fitting to the external fitting portion 122 of the first frame body 12.

Figure 11:
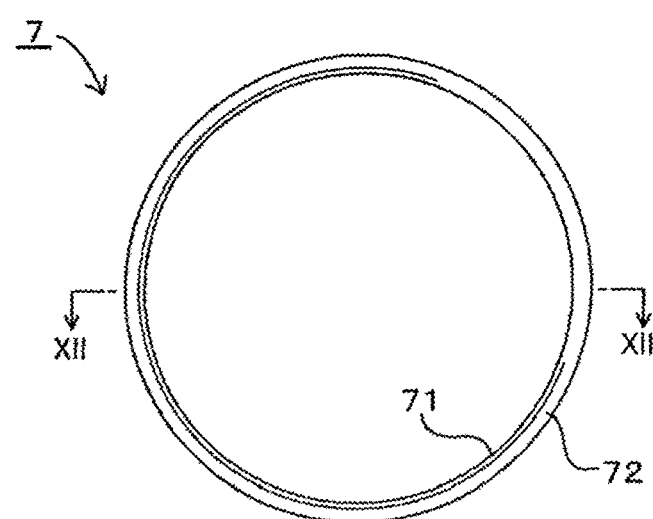
FIG. 11 is a bottom view of a cap body.
Figure 12:
FIG. 12 is a sectional view along line XII-XII in FIG. 11.
Figure 12:

In some aspects, preferably, the first-type frame body 1 at the upper layer is closed by a cap body 7 to cover the first internal space 11. The cap body 7 is illustrated in FIG. 11 and FIG. 12. FIG. 11 is a bottom view of the cap body 7. FIG. 12 is a sectional view along line XII-XII in FIG. 11. The cap body 7 is a circular plate body in plan view and includes, at a lower portion thereof, an annular external fitting portion 72 having an internal thread 71. The external fitting portion 72 has dimensions that enable external fitting to the internal fitting portion 124 of the first frame body 12.

A microorganism culture apparatus 100A, having the aforementioned configuration, allows for the circulation of a nutrient-containing liquid in the first internal space 11 of the first-type frame body 1 at the upper layer to supply a nutrient from the upper side to a microorganism in the first internal space 11 of the first-type frame body 1 at the lower layer, and it is thus possible to culture the microorganism.

In some aspects, instead of a nutrient-containing liquid, a nutrient-containing gas, an environmental component-containing gas, or an environmental component-containing liquid may be circulated in the first internal space 11 of the first-type frame body 1 at the upper layer. When an environmental component-containing gas or an environmental component-containing liquid is circulated, it is possible to supply an environmental component from the upper side to a microorganism in the first internal space 11 of the first-type frame body 1 at the lower layer, and it is thus possible to culture the microorganism.

Thus, when using microorganism culture apparatus 100A, one may culture a microorganism with minimal difficulty, and, moreover, it is possible to easily change the type, the concentration, and the like of a nutrient or an environmental component that is to be supplied. Therefore, it is possible to implement various culture conditions and to study various microorganisms that are difficult to be cultured using traditional methods.

A microorganism culture kit 10A according to the present embodiment can provide various benefits. The microorganism culture apparatus 100A having a two-layer stack structure, such as that illustrated in FIG. 7, can be configured. A microorganism culture apparatus having a simple configuration can be realized due to including only the two first-type frame bodies 1. The microorganism culture apparatus 100A can be configured by only the two first-type frame bodies 1 being simply coupled to each other by a screw mechanism that uses an internal thread and an external thread, and therefore, it is possible to improve efficiency in the production of the apparatus, and it is thus possible to start culture work of a microorganism easily. Each of the first-type frame bodies 1 is formed by the annular first frame body 12 surrounding the first internal space 11 and thus has a simple configuration. That is, the microorganism culture kit 10A according to the present embodiment is formed by simple components.

Figure 13:
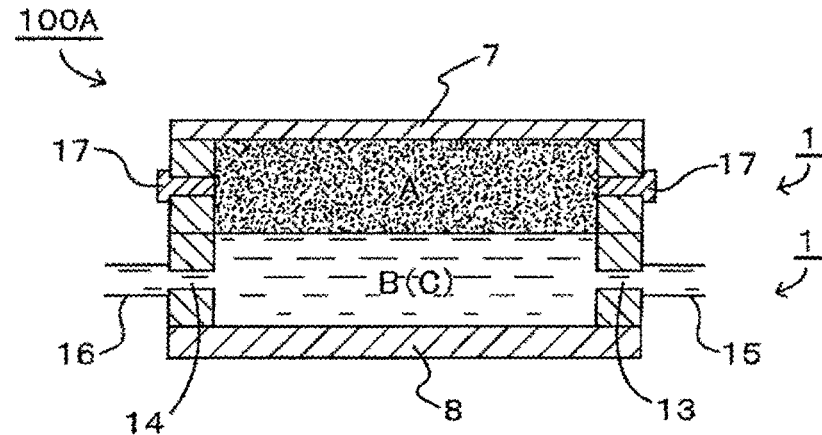
FIG. 13 is a schematic sectional view illustrating a first modification of the microorganism culture apparatus constituted by the microorganism culture kit according to the first embodiment.

As illustrated in FIG. 13, in some aspects the upper layer and the lower layer may be reversed as compared with the apparatus in FIG. 7. In this case, it is possible to supply a nutrient or an environmental component from the lower side to a microorganism in the first internal space 11 of the first-type frame body 1 at the upper layer, and it is thus possible to culture the microorganism.

In some aspects, preferably, one of the first-type frame bodies 1 is provided with one or more types of sensors that detect a culture state. The sensors may be selected from a temperature sensor, a pH sensor, and a gas concentration sensor. In some aspects, preferably, one or more types of stimulation apply portions that apply physical stimulation to a microorganism-containing medium from outside is attached to the same one of the first-type frame bodies 1. One of the first-type frame bodies may be used to hold a microorganism-containing medium.

Figure 14:
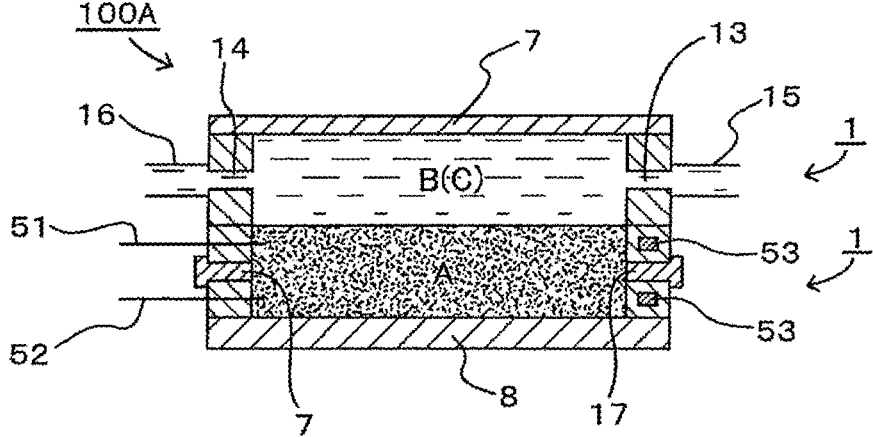
FIG. 14 is a schematic sectional view illustrating a second modification of the microorganism culture apparatus constituted by the microorganism culture kit according to the first embodiment.

For example, in the microorganism culture apparatus 100A illustrated in FIG. 14, the first-type frame body 1 at the lower layer is provided with a temperature sensor 51, a pH sensor 52, and an ultrasonic wave oscillator 53. In this case, a culture state of a microorganism can be detected by the temperature sensor 51 and the pH sensor 52 and monitored by an external device (not illustrated), and it is thus possible to determine the culture state rapidly and appropriately. Moreover, at least one of the type and the concentration of a nutrient-containing liquid, a nutrient-containing gas, an environmental component-containing gas, or an environmental component-containing liquid that is circulated in the first-type frame body 1 at the upper layer can be changed on the basis of a result of monitoring, and it is thus possible to realize culture conditions suitable for a microorganism easily even in the middle of culture.

Figure 15:
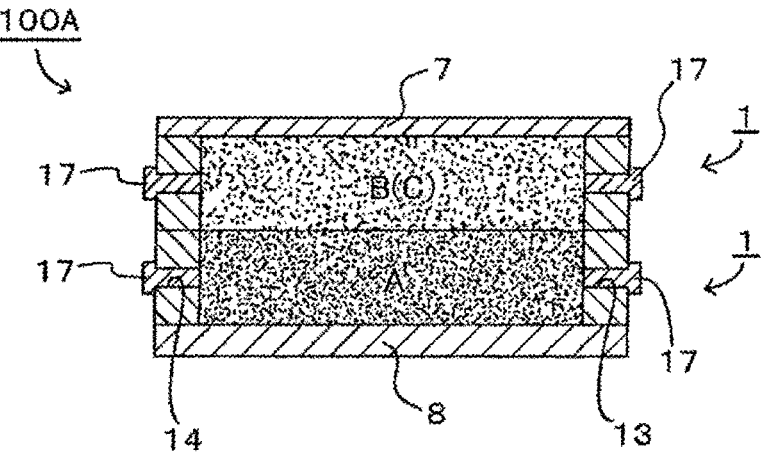
FIG. 15 is a schematic sectional view illustrating a third modification of the microorganism culture apparatus constituted by the microorganism culture kit according to the first embodiment.

In some aspects, both of the two first-type frame bodies 1 may be used in a state in which the inflow passage 13 and the outflow passage 14 are closed. For example, in the microorganism culture apparatus 100A illustrated in FIG. 15, the first-type frame bodies 1 in the state in which the inflow passage 13 and the outflow passage 14 are closed are disposed at the upper layer and the lower layer. In this case, one (at the lower layer, for example) of the first-type frame bodies 1 holds a microorganism-containing medium, and the other (at the upper layer, for example) of the first-type frame bodies 1 holds a nutrient-containing material or an environmental component-containing material. Thus, it is also possible to supply a nutrient or an environmental component to a microorganism in the first internal space 11 of the one of the first-type frame bodies 1 from the other of the first-type frame bodies 1, and it is thus possible to culture the microorganism.

Figure 16:
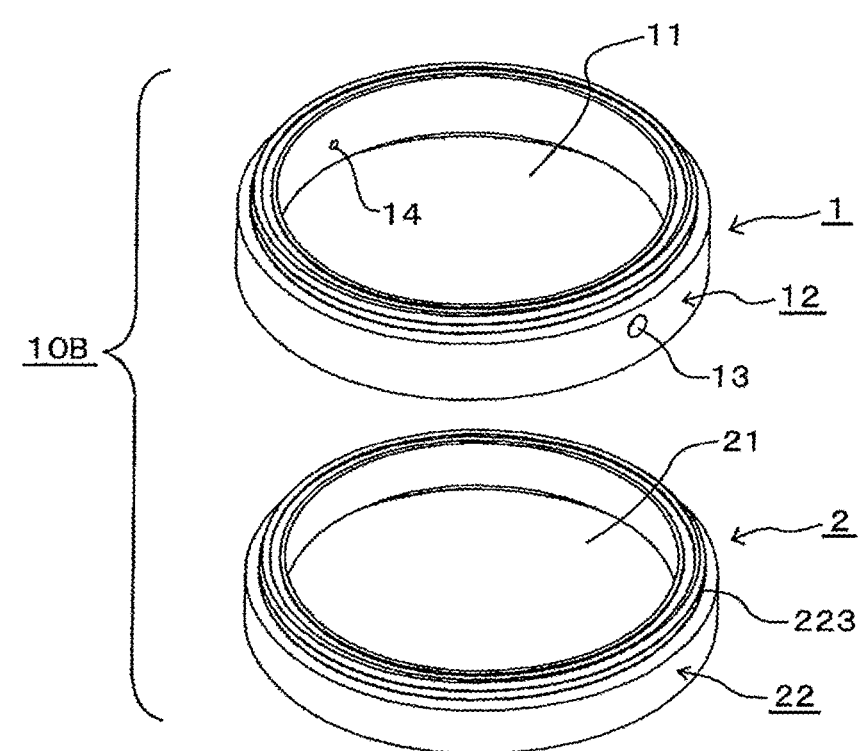
FIG. 16 is a perspective view illustrating a microorganism culture kit according to a second embodiment of the present invention.

In some aspects, the microorganism culture kit according to the present embodiment includes two frame bodies stackable on each other. As illustrated in FIG. 16, the two frame bodies are the first-type frame body 1 and a second-type frame body 2 in a microorganism culture kit 10B according to the present embodiment.

Figure 17:
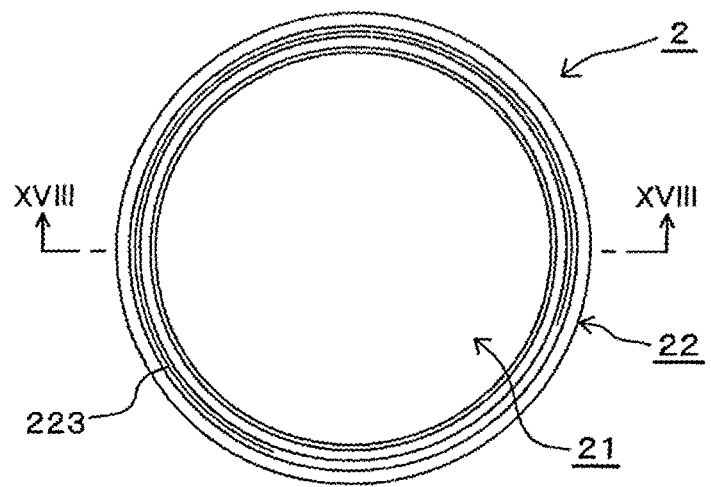
FIG. 17 is a plan view illustrating a second-type frame body of a microorganism culture kit.
Figure 18:
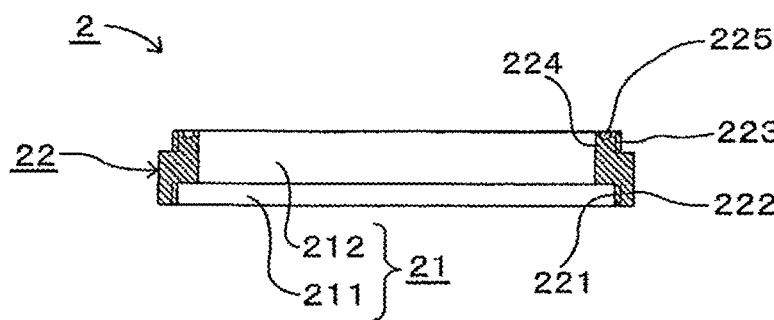
FIG. 18 is a sectional view along line XVIII-XVIII in FIG. 17.

FIG. 17 is a plan view of the second-type frame body 2. FIG. 18 is a sectional view along line XVIII-XVIII in FIG. 17. The second-type frame body 2 includes an annular second frame body 22 surrounding a second internal space 21. As illustrated in FIG. 18, the second frame body 22 includes, at a lower portion thereof, an annular external fitting portion 222 having an internal thread 221 and includes, at an upper portion thereof, an annular internal fitting portion 224 having an external thread 223. The external fitting portion 222 has dimensions that enable external fitting to the internal fitting portion 224 and the internal fitting portion 124 of the first-type frame body 1. The internal fitting portion 224 has dimensions that enable internal fitting to the external fitting portion 222 and the external fitting portion 122 of the first-type frame body 1. The second internal space 21 includes an internal space 211 surrounded by the external fitting portion 222 and an internal space 212 other than the internal space 211. The internal fitting portion 224 includes an O-ring 225 at the upper surface thereof The first-type frame body 1 is the same as the first-type frame body 1 according to the first embodiment. The external fitting portion 122 of the first-type frame body 1 has dimensions that enable external fitting to the internal fitting portion 224 of the second-type frame body 2, and the internal fitting portion 124 of the first-type frame body 1 has dimensions that enable internal fitting to the external fitting portion 222 of the second-type frame body 2.

Figure 19:
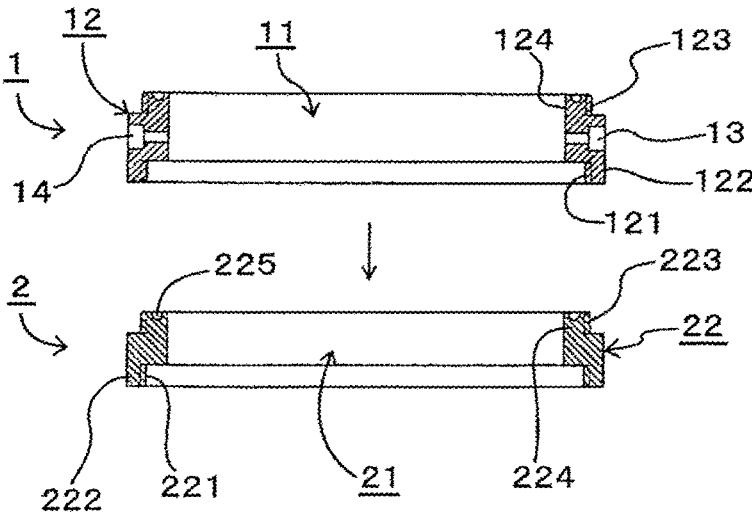
FIG. 19 is a sectional view illustrating work of coupling a first-type frame body and a second-type frame body to each other.

As illustrated in, for example, FIG. 19, the first-type frame body 1 and the second-type frame body may be configured to be stacked on and coupled to each other as a result of the internal thread 121 of the first-type frame body 1 positioned at an upper location being screwed with the external thread 223 of the second-type frame body 2 positioned at a lower location. In this case, the first-type frame body 1 and the second-type frame body 2 coupled to each other may be sealed by the O-ring 225.

The second-type frame body 2 may be capable of holding, in the second internal space 21, a microorganism-containing medium, a nutrient-containing material, or an environmental component-containing material.

Figure 20:
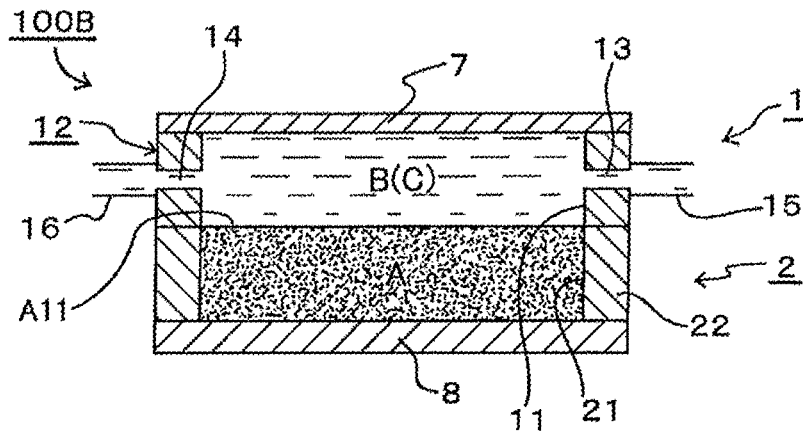
FIG. 20 is a schematic sectional view illustrating a first modification of a microorganism culture apparatus constituted by the microorganism culture kit according to the second embodiment.

A microorganism culture kit 10B according to the present embodiment provides several benefits. As illustrated in FIG. 20, a two-layer stack structure body can be constructed by the first-type frame body 1 and the second-type frame body 2 being stacked on each other, and the two-layer stack structure body is usable as the microorganism culture apparatus 100B. In the two-layer stack structure body, the second-type frame body 2 is disposed at the lower layer, and the first-type frame body 1 in a state in which the inflow passage 13 and the outflow passage 14 are open is disposed at the upper layer. In some aspects, preferably, a membrane filter (not illustrated) is disposed between the first-type frame body 1 at the upper layer and the second-type frame body 2 at the lower layer. The microorganism culture apparatus 100B may configured such that the second-type frame body 2 at the lower layer holds a microorganism-containing medium in the second internal space 21 and the first-type frame body 1 at the upper layer circulates a nutrient-containing liquid in the first internal space 11. That is, the microorganism culture apparatus 100B may have a two-layer stack structure formed by the layer-like culture portion A formed by the second-type frame body 2 that is at the lower layer and that holds the microorganism-containing medium, and the layer-like nutrient supply portion B formed by the first-type frame body 1 that is at the upper layer and that is disposed at the first surface A11 of the culture portion A, the nutrient supply portion B supplying a nutrient to the culture portion A.

In some aspects, the second-type frame body 2 at the lower layer is stacked on the base 8. In some aspects, preferably, the first-type frame body 1 at the upper layer is closed by the cap body 7. The cap body 7 and the base 8 are the same as the cap body 7 and the base 8 used in the first embodiment. The external fitting portion 72 of the cap body 7 has dimensions that enable external fitting to the internal fitting portion 224 of the second-type frame body 2, and the internal fitting portion 82 of the base 8 has dimensions that enable internal fitting to the external fitting portion 222 of the second-type frame body 2.

A microorganism culture apparatus 100B, having the aforementioned configuration, is able to circulate a nutrient-containing liquid in the first internal space 11 of the first-type frame body 1 at the upper layer to supply a nutrient from the upper side to a microorganism in the second internal space 21 of the second-type frame body 2 at the lower layer, and it is thus possible to culture the microorganism.

Instead of a nutrient-containing liquid, a nutrient-containing gas, an environmental component-containing gas, or an environmental component-containing liquid may be circulated in the first internal space 11 of the first-type frame body 1 at the upper layer. When an environmental component-containing gas or an environmental component-containing liquid is circulated, it is possible to supply an environmental component from the upper side to a microorganism in the second internal space 21 of the second-type frame body 2 at the lower layer, and it is thus possible to culture the microorganism.

Thus, according to the microorganism culture apparatus 100B, it is possible to culture a microorganism with minimal difficulty, and, moreover, it is possible to easily change the type, the concentration, and the like of a nutrient or an environmental component that is to be supplied. Therefore, it is possible to replicate various culture conditions and study various microorganisms that are difficult to be cultured using traditional methods.

The microorganism culture kit 10B according to the present embodiment can provide various benefits. The microorganism culture apparatus 100B having a two-layer stack structure, such as that illustrated in FIG. 20, can be configured. A microorganism culture apparatus having a simple configuration can be realized due to including only the first-type frame body 1 and the second-type frame body 2. The microorganism culture apparatus 100B can be configured by only the first-type frame body 1 and the second-type frame body 2 being coupled to each other by a screw mechanism that uses an internal thread and an external thread, and therefore, it is possible to improve efficiency in the production of the apparatus, and it is thus possible to start culture work of a microorganism easily. Each of the first-type frame body 1 and the second-type frame body 2 may be formed by an annular frame body surrounding an internal space and thus has a simple configuration. That is, the microorganism culture kit 10B according to the present embodiment is formed by simple components.

Figure 21:
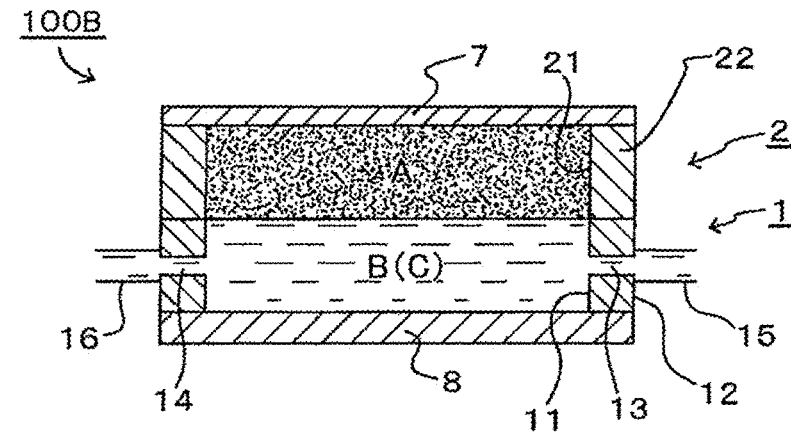
FIG. 21 is a schematic sectional view illustrating a second modification of the microorganism culture apparatus constituted by the microorganism culture kit according to the second embodiment.

As illustrated in FIG. 21, in some aspects the upper layer and the lower layer may be reversed as compared with the apparatus in FIG. 20. In this case, it is possible to supply a nutrient or an environmental component from the lower side to a microorganism in the second internal space 21 of the second-type frame body 2 at the upper layer, and it is thus possible to culture the microorganism.

Figure 22:
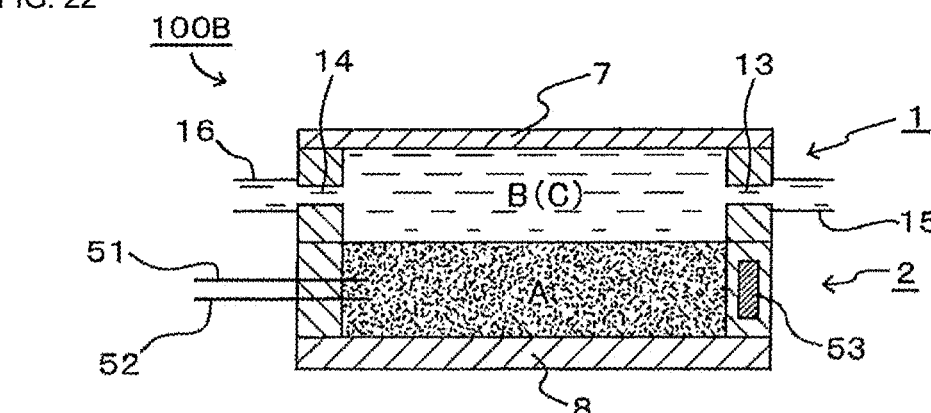
FIG. 22 is a schematic sectional view illustrating a third modification of the microorganism culture apparatus constituted by the microorganism culture kit according to the second embodiment.

In some aspects, the second-type frame body 2 is provided with one or more types of sensors configured to detect a culture state. The sensors may be selected from a temperature sensor, a pH sensor, and a gas concentration sensor. In some aspects, the sensors may be configured to monitor or detect the state of a microorganism-containing medium and are attached to the second-type frame body 2. The second-type frame body 2 may be used to hold the microorganism-containing medium. For example, in the microorganism culture apparatus 100B illustrated in FIG. 22, the second-type frame body 2 at the lower layer is provided with the temperature sensor 51, the pH sensor 52, and the ultrasonic wave oscillator 53. In this case, a culture state of a microorganism can be detected by the temperature sensor 51 and the pH sensor 52 and monitored by an external device (not illustrated), and it is thus possible to determine the culture state rapidly and appropriately. Moreover, at least one of the type and the concentration of a nutrient-containing liquid, a nutrient-containing gas, an environmental component-containing gas, or an environmental component-containing liquid that is circulated in the first-type frame body 1 at the upper layer can be changed on the basis of a result of monitoring, and it is thus possible to replicate culture conditions suitable for a microorganism easily even in the middle of culture.

Figure 23:
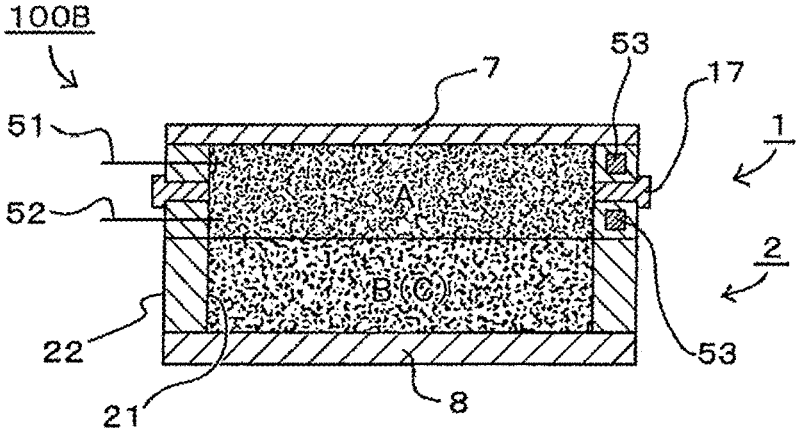
FIG. 23 is a schematic sectional view illustrating a fourth modification of the microorganism culture apparatus constituted by the microorganism culture kit according to the second embodiment.

As illustrated in FIG. 23, the first-type frame body 1 may be used in a state in which the inflow passage 13 and the outflow passage 14 are closed while one of the first-type frame body 1 and the second-type frame body 2 holds a microorganism-containing medium and the other of the first-type frame body 1 and the second-type frame body 2 holds a nutrient-containing material or an environmental component-containing material. When the first-type frame body 1 holds a microorganism-containing medium, the first-type frame body 1 may be provided with the temperature sensor 51, the pH sensor 52, and the ultrasonic wave oscillator 53.

Figure 24:
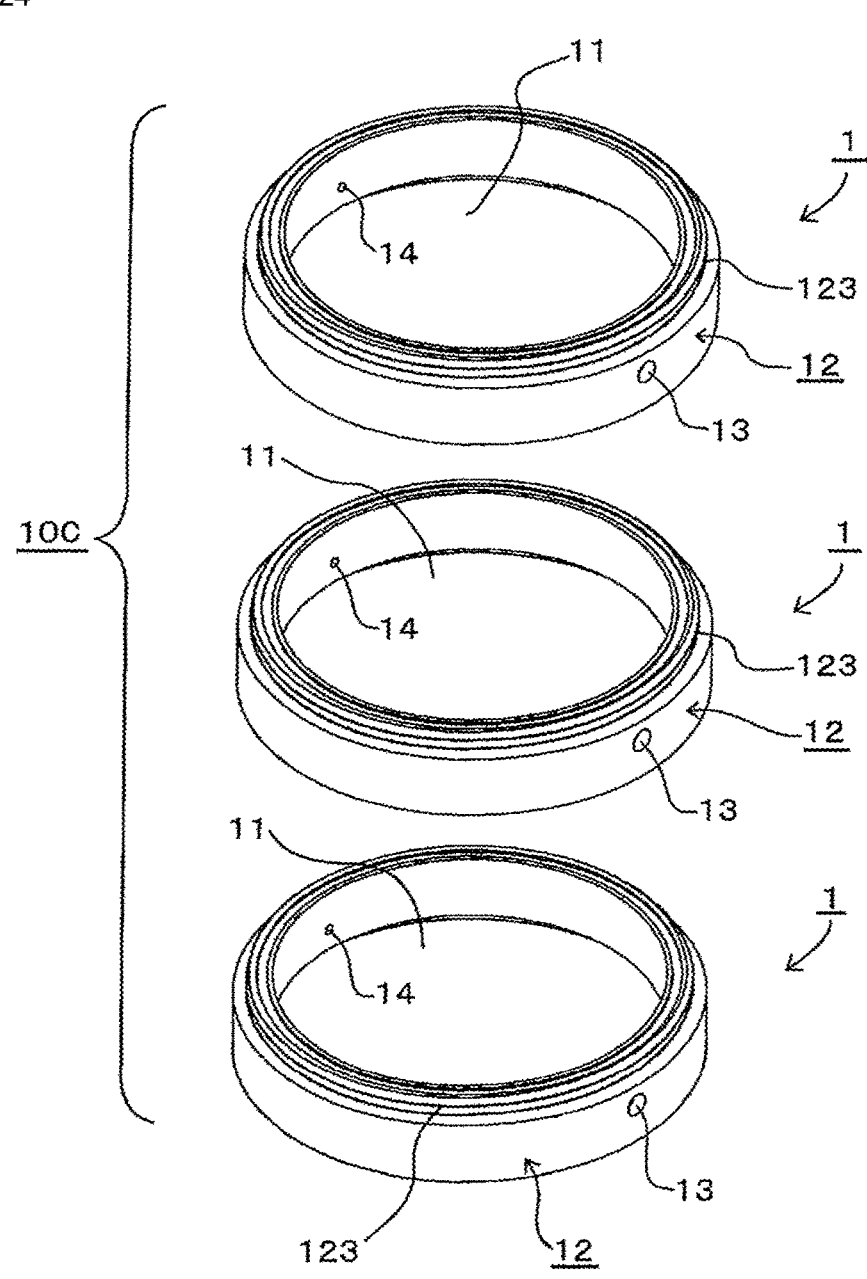
FIG. 24 is a perspective view illustrating an example of a microorganism culture kit according to a third embodiment of the present invention.
Figure 25:
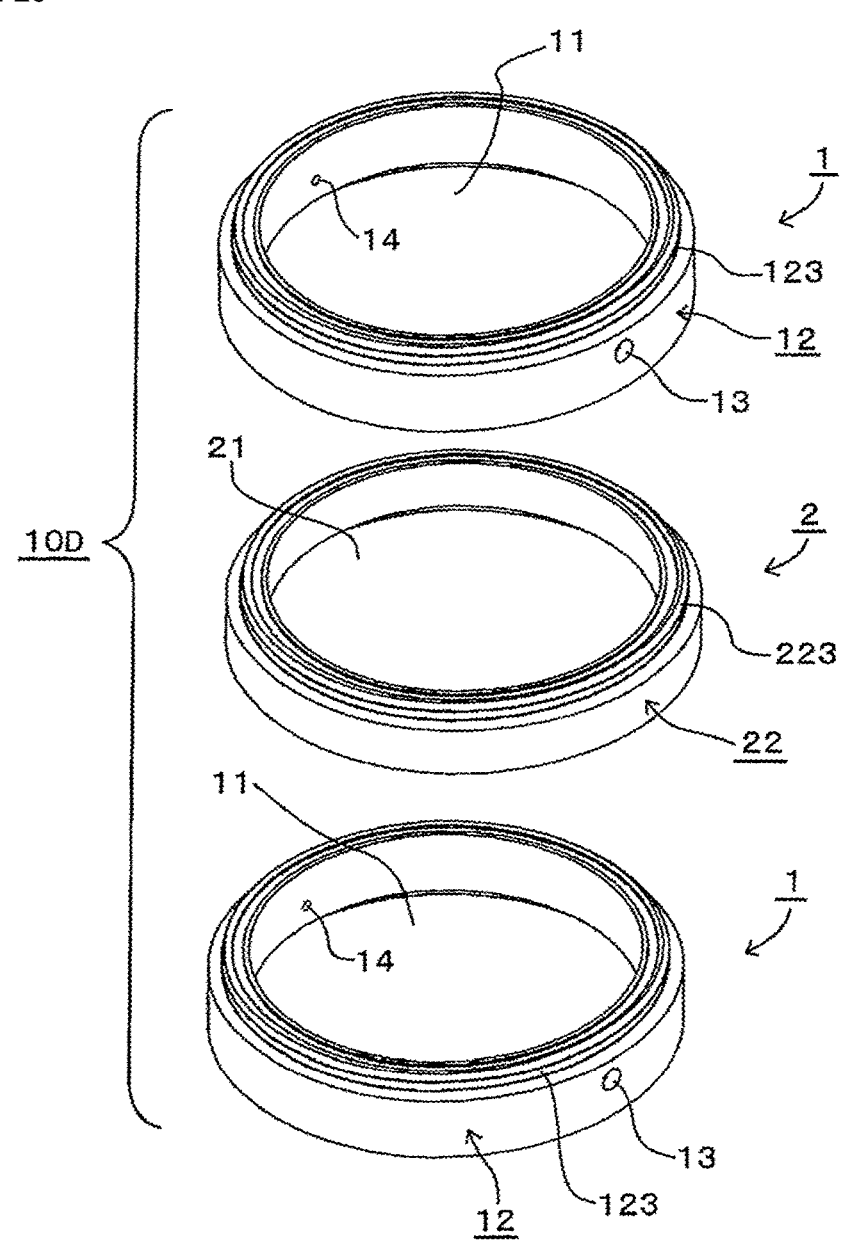
FIG. 25 is a perspective view illustrating another example of the microorganism culture kit according to the third embodiment of the present invention.

A microorganism culture kit according to the present embodiment further includes one frame body additionally in the microorganism culture kit 10A according to the first embodiment. The additional one frame body is the first-type frame body 1 or the second-type frame body 2. That is, the microorganism culture kit according to the present embodiment includes a microorganism culture kit 10C including, as illustrated in FIG. 24, three first-type frame bodies 1 and a microorganism culture kit 10D including, as illustrated in FIG. 25, two first-type frame bodies 1 and one second-type frame body 2. The first-type frame body 1 is the same as the first-type frame body 1 in the first embodiment, and the second-type frame body 2 is the same as the second-type frame body 2 in the second embodiment.

Figure 26:
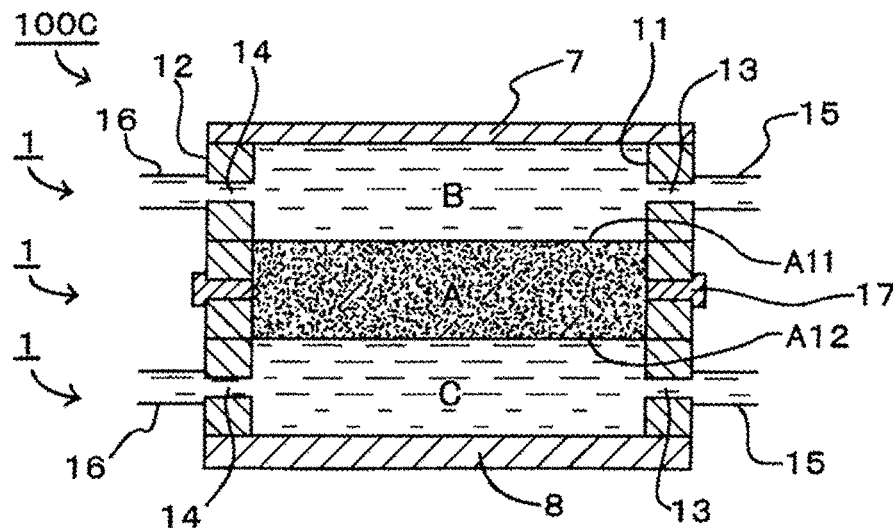
FIG. 26 is a schematic sectional view illustrating a microorganism culture apparatus constituted by the microorganism culture kit in FIG. 24.

The microorganism culture kit 10C according to the present embodiment may be used as follows. As illustrated in FIG. 26, a three-layer stack structure body may be configured by three first-type frame bodies 1 being stacked on each other, and the three-layer stack structure body is usable as a microorganism culture apparatus 100C. In the three-layer stack structure body, the first-type frame bodies 1 in a state in which the inflow passage 13 and the outflow passage 14 are open and are disposed at the upper layer and the lower layer, and the first-type frame body 1 in a state in which the inflow passage 13 and the outflow passage 14 are closed is disposed at an intermediate layer. Preferably, a membrane filter (not illustrated) is disposed between the layers. The microorganism culture apparatus 100C may be configured such that the first-type frame body 1 at the intermediate layer holds a microorganism-containing medium in the first internal space 11, the first-type frame body 1 at the upper layer circulates a nutrient-containing liquid in the first internal space 11, and the first-type frame body 1 at the lower layer circulates an environmental component-containing liquid in the first internal space 11. That is, the microorganism culture apparatus 100C has a three-layer stack structure formed by the layer-like culture portion A formed by the first-type frame body 1 that is at the intermediate layer and that holds the microorganism-containing medium, the layer-like nutrient supply portion B formed by the first-type frame body 1 that is at the upper layer and that is disposed at the first surface A11 of the culture portion A, the nutrient supply portion B supplying a nutrient to the culture portion A, and a layer-like environmental component supply portion C formed by the first-type frame body 1 that is at the lower layer and that is disposed at a second surface A12 of the culture portion A, the environmental component supply portion C supplying an environmental component to the culture portion A.

The three first-type frame bodies 1 may be stacked on and coupled to each other as a result of the internal thread 121 of the first-type frame body 1 positioned at an upper location being screwed with the external thread 123 of the first-type frame body 1 positioned at a lower location. The first-type frame bodies 1 coupled to each other are sealed by the O-ring 125.

In some aspects, preferably, the first-type frame body 1 at the lower layer is stacked on the base 8. Preferably, the first-type frame body 1 at the upper layer is closed by the cap body 7. The cap body 7 and the base 8 are the same as the cap body 7 and the base 8 used in the first embodiment and the second embodiment.

A microorganism culture apparatus 100C having the aforementioned configuration allows for the circulation of a nutrient-containing liquid in the first internal space 11 of the first-type frame body 1 at the upper layer and circulating an environmental component-containing liquid in the first internal space 11 of the first-type frame body 1 at the lower layer to supply a nutrient from the upper side and an environmental component from the lower side to a microorganism in the first internal space 11 of the first-type frame body 1 at the intermediate layer, and it is thus possible to culture the microorganism.

Instead of a nutrient-containing liquid, a nutrient-containing gas, an environmental component-containing gas, or an environmental component-containing liquid may be circulated in the first internal space 11 of the first-type frame body 1 at the upper layer. When an environmental component-containing gas or an environmental component-containing liquid is circulated, it is possible to supply an environmental component also from the upper side to a microorganism in the first internal space 11 of the first-type frame body 1 at the intermediate layer, and it is thus possible to culture the microorganism.

Instead of an environmental component-containing liquid, an environmental component-containing gas, a nutrient-containing gas, or a nutrient-containing liquid may be circulated in the first internal space 11 of the first-type frame body 1 at the lower layer. When a nutrient-containing gas or a nutrient-containing liquid is circulated, it is possible to supply a nutrient also from the lower side to a microorganism in the first internal space 11 of the first-type frame body 1 at the intermediate layer, and it is thus possible to culture the microorganism.

The microorganism culture kit 10C according to the present embodiment provides several benefits. The microorganism culture apparatus 100C having a three-layer stack structure, such as that illustrated in FIG. 26, can be configured. A microorganism culture apparatus having a simple configuration can be realized due to including only the three first-type frame bodies 1. The microorganism culture apparatus 100C can be configured by only the three first-type frame bodies 1 being simply coupled to each other by a screwing mechanism that uses an internal thread and an external thread, and therefore, it is possible to improve efficiency in the production of the apparatus, and it is thus possible to start culture work of a microorganism easily. Each of the first-type frame bodies 1 is an annular frame body surrounding an internal space and thus has a simple configuration. That is, the microorganism culture kit 10C according to the present embodiment is formed by simple components.

Figure 27:
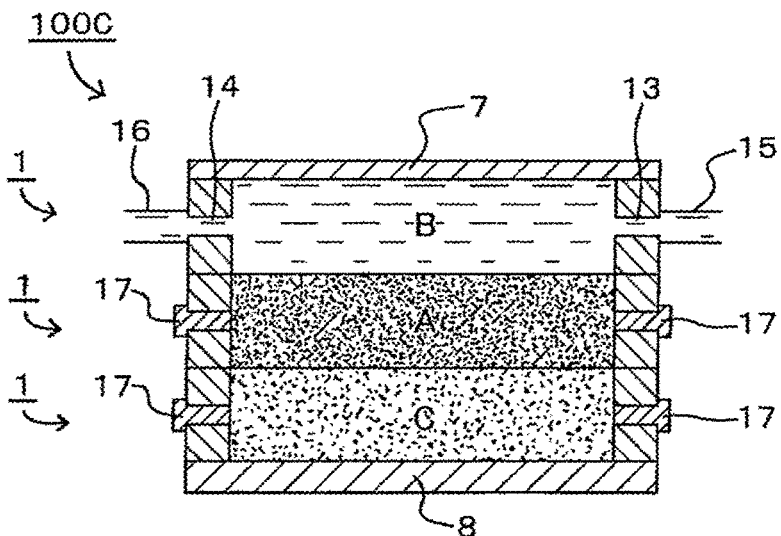
FIG. 27 is a schematic sectional view illustrating a first modification of the microorganism culture apparatus constituted by the microorganism culture kit in FIG. 24.

In the microorganism culture apparatus 100C, not only the first-type frame body 1 disposed at the intermediate layer but also the first-type frame body 1 disposed at at least one of the upper layer and the lower layer may be used in a state in which the inflow passage 13 and the outflow passage 14 are closed. In the microorganism culture apparatus 100C illustrated in FIG. 27, the first-type frame body 1 at the lower layer is also used in a state in which the inflow passage 13 and the outflow passage 14 are closed. The first-type frame body 1 at the intermediate layer holds a microorganism-containing medium, the first-type frame body 1 at the upper layer circulates a nutrient-containing liquid or a nutrient-containing gas, and the first-type frame body 1 at the lower layer holds an environmental component-containing material. Thus, it is also possible to supply a nutrient from the upper side and supply an environmental component from the lower side to a microorganism in the first internal space 11 of the first-type frame body 1 at the intermediate layer, and it is thus possible to culture the microorganism. In FIG. 27, the first-type frame body 1 at the upper layer may circulate an environmental component-containing liquid or an environmental component-containing gas while the first-type frame body 1 at the lower layer holds a nutrient-containing material.

Figure 28:
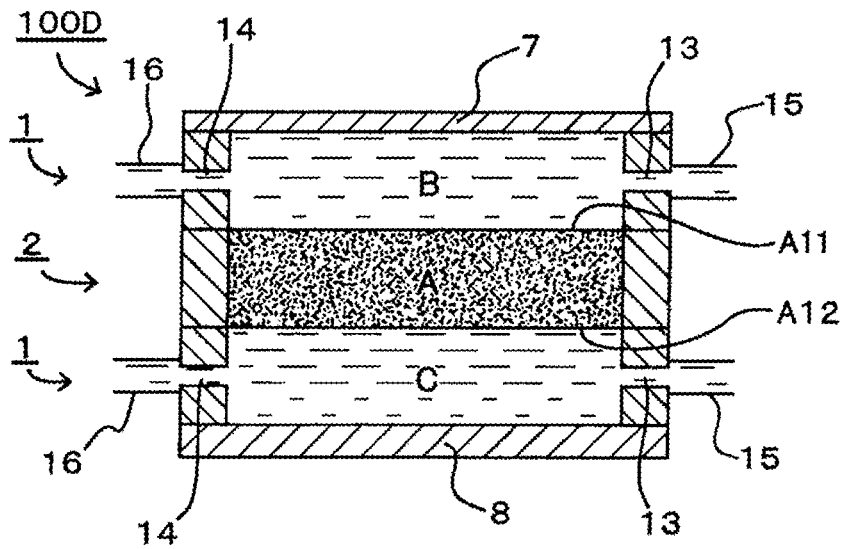
FIG. 28 is a schematic sectional view illustrating a microorganism culture apparatus constituted by the microorganism culture kit in FIG. 25.

The microorganism culture kit 10D according to the present embodiment is usable as follows. As illustrated by FIG. 28, a three-layer stack structure body can be configured by the first-type frame bodies 1 being stacked on the upper and lower side of the second-type frame body 2, and the three-layer stack structure body is usable as a microorganism culture apparatus 100D. In the three-layer stack structure body, the first-type frame bodies 1 in a state in which the inflow passage 13 and the outflow passage 14 are open are disposed at the upper layer and the lower layer, and the second-type frame body 2 is disposed at the intermediate layer. Preferably, a membrane filter (not illustrated) is disposed between the layers. The microorganism culture apparatus 100D is configured such that the second-type frame body 2 at the intermediate layer holds a microorganism-containing medium in the second internal space 21, the first-type frame body 1 at the upper layer circulates a nutrient-containing liquid in the first internal space 11, and the first-type frame body 1 at the lower layer circulates an environmental component-containing liquid in the first internal space 11. That is, the microorganism culture apparatus 100D has a three-layer stack structure formed by the layer-like culture portion A formed by the second-type frame body 2 that is at the intermediate layer and that holds the microorganism-containing medium, the layer-like nutrient supply portion B formed by the first-type frame body 1 that is at the upper layer and that is disposed at the first surface All of the culture portion A, the nutrient supply portion B supplying a nutrient to the culture portion A, and a layer-like environmental component supply portion C formed by the first-type frame body 1 that is at the lower layer and that is disposed at a second surface A12 of the culture portion A, the environmental component supply portion C supplying an environmental component to the culture portion A.

The first-type frame body 1 and the second-type frame body 2 can be stacked on and coupled to each other as a result of the internal thread 121 of the first-type frame body 1 positioned at an upper location being screwed with the external thread 223 of the second-type frame body 2 positioned at a lower location, the first-type frame body 1 and the second-type frame body 2 being sealed by the O-ring 225, and the second-type frame body 2 and the first-type frame body 1 can be stacked on and coupled to each other as a result of the internal thread 221 of the second-type frame body 2 positioned at an upper location being screwed with the external thread 123 of the first-type frame body 1 positioned at a lower location, the second-type frame body 2 and the first-type frame body 1 being sealed by the O-ring 125.

In some aspects, preferably, the first-type frame body 1 at the lower layer is stacked on the base 8. The the first-type frame body 1 at the upper layer may be closed by the cap body 7. The cap body 7 and the base 8 are the same as the cap body 7 and the base 8 used in the first embodiment and the second embodiment.

A microorganism culture apparatus 100D having the aforementioned configuration it capable of circulating a nutrient-containing liquid in the first internal space 11 of the first-type frame body 1 at the upper layer and circulating an environmental component-containing liquid in the first internal space 11 of the first-type frame body 1 at the lower layer to supply a nutrient from the upper side and supply an environmental component from the lower side to a microorganism in the second internal space 21 of the second-type frame body 2 at the intermediate layer, and it is thus possible to culture the microorganism.

Instead of a nutrient-containing liquid, a nutrient-containing gas, an environmental component-containing gas, or an environmental component-containing liquid may be circulated in the first internal space 11 of the first-type frame body 1 at the upper layer. When an environmental component-containing gas or an environmental component-containing liquid is circulated, it is possible to supply an environmental component also from the upper side to a microorganism in the second internal space 21 of the second-type frame body 2 at the intermediate layer, and it is thus possible to culture the microorganism.

Instead of an environmental component-containing liquid, an environmental component-containing gas, a nutrient-containing gas, or a nutrient-containing liquid may be circulated in the first internal space 11 of the first-type frame body 1 at the lower layer. When a nutrient-containing gas or a nutrient-containing liquid is circulated, it is possible to supply a nutrient also from the lower side to a microorganism in the second internal space 21 of the second-type frame body 2 at the intermediate layer, and it is thus possible to culture the microorganism.

The microorganism culture kit 10D according to the present embodiment can exert the following effects. (a) The microorganism culture apparatus 100D having a three-layer stack structure, such as that illustrated in FIG. 28, can be configured. (b) A microorganism culture apparatus having a simple configuration can be realized due to including only the two first-type frame bodies 1 and the one second-type frame body 2. (c) The microorganism culture apparatus 100D can be configured by only the two first-type frame bodies 1 and the one second-type frame body 2 being coupled to each other by a screw mechanism that uses an internal thread and an external thread, and therefore, it is possible to improve efficiency in the production of the apparatus, and it is thus possible to start culture work of a microorganism easily. (d) Each of the first-type frame body 1 and the second-type frame body 2 is an annular frame body surrounding an internal space and thus has a simple configuration. That is, the microorganism culture kit 10D according to the present embodiment is formed by simple components.

Figure 29:
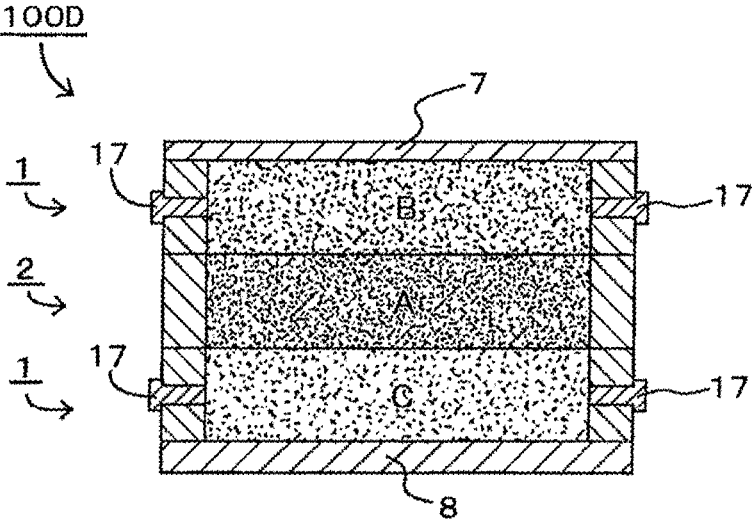
FIG. 29 is a schematic sectional view illustrating a first modification of the microorganism culture apparatus constituted by the microorganism culture kit in FIG. 25.

In the microorganism culture apparatus 100D, the first-type frame body 1 disposed at at least one of the upper layer and the lower layer may be used in a state in which the inflow passage 13 and the outflow passage 14 are closed. In the microorganism culture apparatus 100D illustrated in FIG. 29, the first-type frame bodies 1 at the upper layer and the lower layer are used in a state in which the inflow passage 13 and the outflow passage 14 are closed. The second-type frame body 2 at the intermediate layer holds a microorganism-containing medium, the first-type frame body 1 at the upper layer holds a nutrient-containing material, and the first-type frame body 1 at the lower layer holds an environmental component-containing material. Thus, it is also possible to supply a nutrient from the upper side and supply an environmental component from the lower side to a microorganism in the second internal space 21 of the second-type frame body 2 at the intermediate layer, and it is thus possible to culture the microorganism. In FIG. 29, the first-type frame body 1 at the upper layer may hold an environmental component-containing material while the first-type frame body 1 at the lower layer holds a nutrient-containing material.

In some aspects, a microorganism culture kit according to the present embodiment further includes one frame body additionally in the microorganism culture kit 10B according to the second embodiment. The additional one frame body may be the first-type frame body 1. That is, the microorganism culture kit according to the present embodiment includes two first-type frame bodies 1 and one second-type frame body 2. Therefore, a microorganism culture kit according to the present embodiment is the same as the microorganism culture kit 10D according to the third embodiment.

Figure 30:
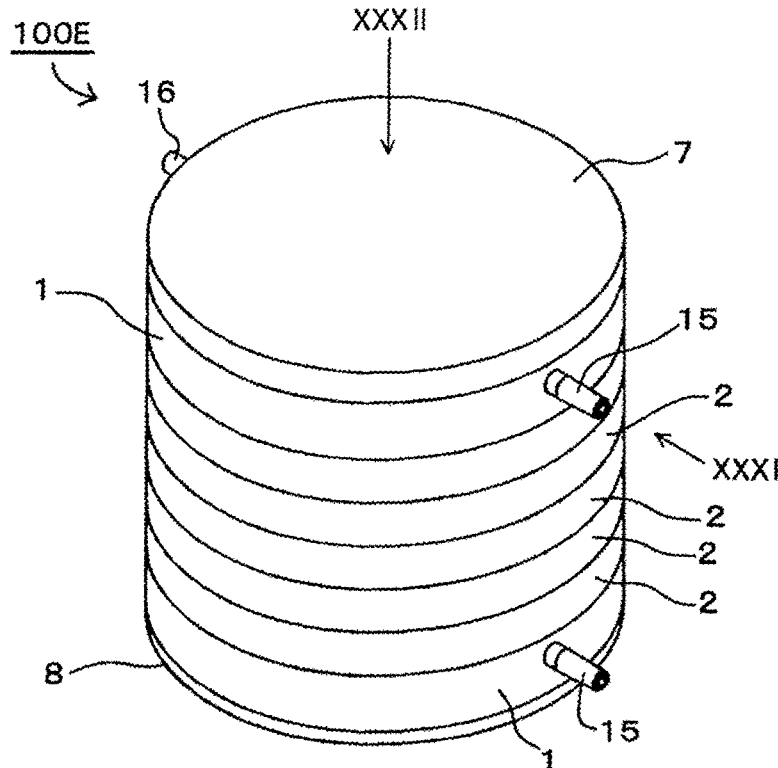
FIG. 30 is a perspective view illustrating an example of a microorganism culture kit according to a fifth embodiment of the present invention.
Figure 31:
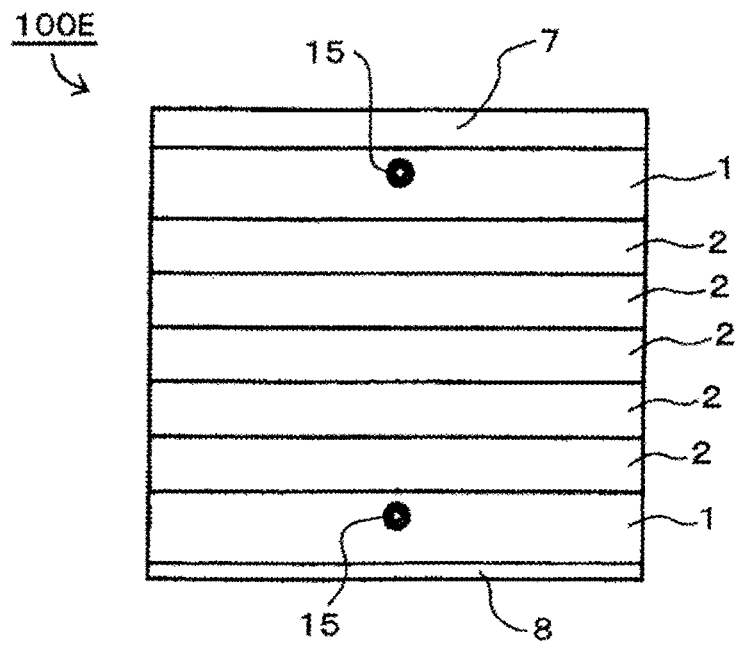
FIG. 31 is a view on arrow XXXI in FIG. 30.
Figure 32:
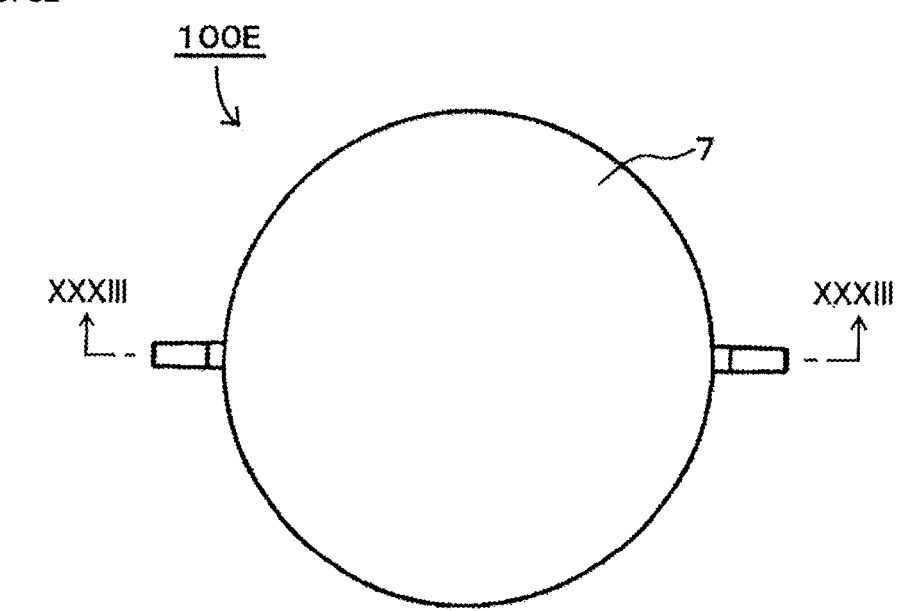
FIG. 32 is a view (plan view) on arrow XXXII in FIG. 30.
Figure 33:
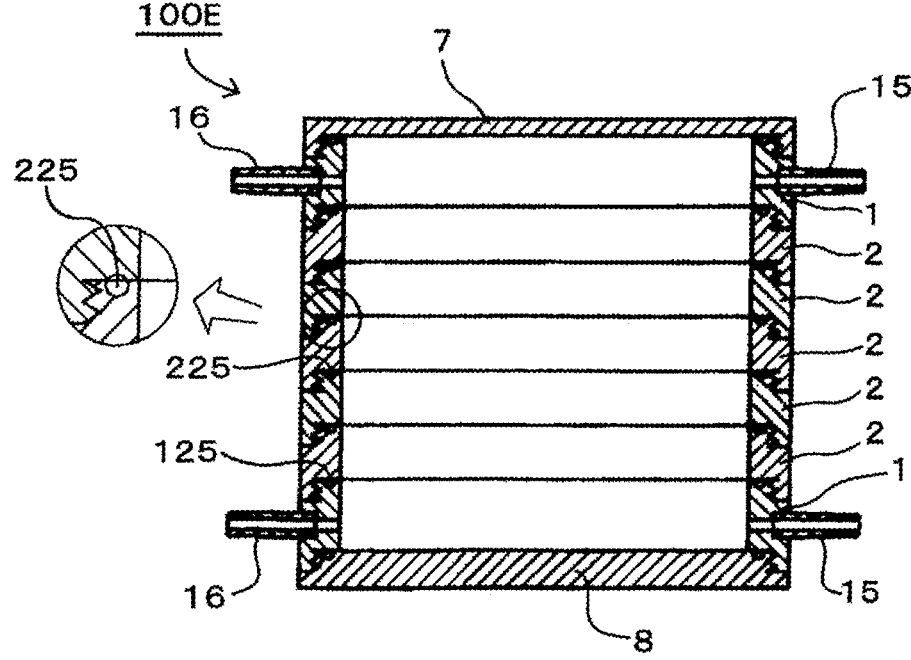
FIG. 33 is a sectional view along line XXXIII-XXXIII in FIG. 32.
Figure 34:
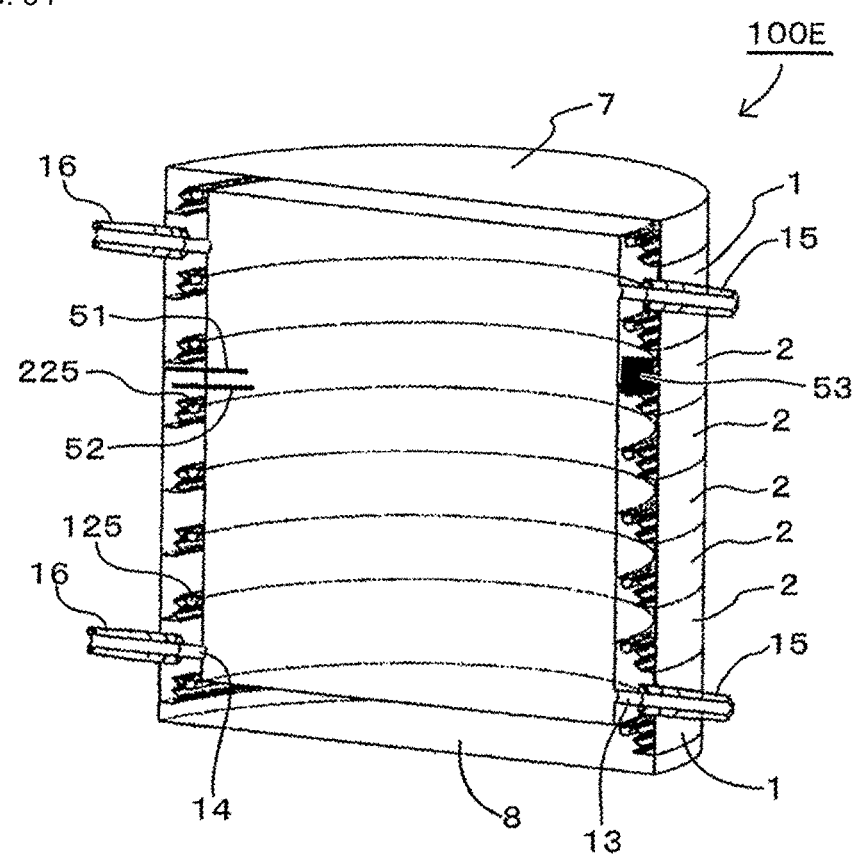
FIG. 34 is a perspective view of the section illustrated in FIG. 32.

In some aspects, a microorganism culture kit according to the present embodiment includes a plurality of microorganism culture kits selected optionally from the microorganism culture kits 10A to 10D according to the first embodiment to the fourth embodiment. Thus, it is possible to configure a multilayer stack structure body by stacking four or more frame bodies on each other, and the multilayer stack structure body is usable as a microorganism culture apparatus. FIG. 30 is a perspective view of a microorganism culture apparatus 100E formed by a seven-layer stack structure body including seven frame bodies stacked on each other. FIG. 31 is a view on arrow XXXI in FIG. 30. FIG. 32 is a view (plan view) on arrow XXXII in FIG. 30. FIG. 33 is a sectional view along line XXXIII-XXXIII in FIG. 32. FIG. 34 is a perspective view of the section illustrated in FIG. 32.

In the seven-layer stack structure body, the lowermost layer (the first layer) may be the first-type frame body 1, the second layer to the sixth layer may be the second-type frame bodies 2, and the uppermost layer (the seventh layer) may be the first-type frame body 1. The first-type frame body 1 at the first layer may be stacked on the base 8, and the first-type frame body 1 at the seventh layer may be closed by the cap body 7.

A microorganism culture apparatus 100E is configured such that the first-type frame body 1 at the first layer circulates an environmental component-containing liquid or an environmental component-containing gas, the second-type frame bodies 2 at the second layer to the fourth layer each hold a microorganism-containing medium, the second-type frame body 2 at the fifth layer holds a nutrient-containing material, and the first-type frame body 1 at the seventh layer circulates a nutrient-containing liquid or a nutrient-containing gas.

Figure 35:
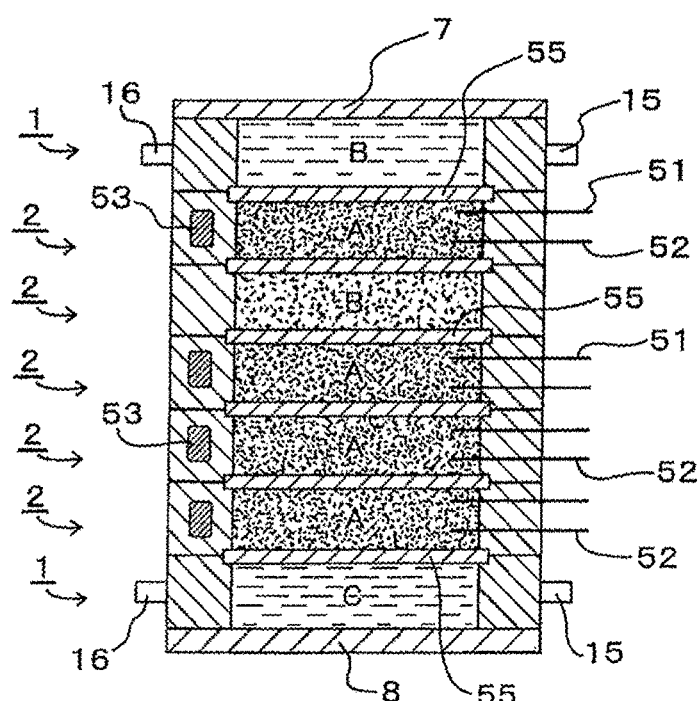
FIG. 35 is a schematic sectional view illustrating a microorganism culture apparatus constituted by the microorganism culture kit according to the fifth embodiment.

That is, as illustrated in FIG. 35, which is a schematic sectional view, the microorganism culture apparatus 100E has a seven-layer stack structure formed by four culture portions A formed by the second-type frame bodies 2 that are at the second layer to the fourth layer and the sixth layer and that each hold a microorganism-containing medium, two nutrient supply portions B that are at the fifth layer and the seventh layer and that each supply a nutrient to the culture portions A, and one environmental component supply portion C that is at the first layer and that supplies an environmental component to the culture portions A. Each of the second-type frame bodies 2 at the second layer to the fourth layer and the sixth layer is provided with the temperature sensor 51, the pH sensor 52, and the ultrasonic wave oscillator 53. A membrane filter 55 is disposed between the layers.

A microorganism culture apparatus 100E provides several benefits. First, it is capable of circulating an environmental component-containing liquid or an environmental component-containing gas in the first-type frame body 1 at the first layer to supply an environmental component from the lower side and supply a nutrient from the upper side to a microorganisms in each of the second-type frame bodies 2 at the second layer to the fourth layer, and it is thus possible to culture the microorganisms in the second-type frame bodies 2 at the second layer to the fourth layer. It is also capable of circulating a nutrient-containing liquid or a nutrient-containing gas in the first-type frame body 1 at the seventh layer to supply a nutrient from the lower side and the upper side to a microorganism in the second-type frame body 2 at the sixth layer, and it is thus possible to culture the microorganism in the second-type frame body 2 at the sixth layer. In some aspects, it is possible to achieve two types of culture conditions due to culture conditions in the stack structure body of the first layer to the fifth layer and culture conditions in the stack structure body of the fifth layer to the seventh layer differ from each other. Therefore, it is possible to improve work efficiency in selection of culture conditions, and it is thus possible to increase the possibility of acquisition of a microorganism that is difficult to be cultured. In the second layer to the fourth layer, the culture portion A has a three-layer structure, and thus, the culture conditions in the layers differ from each other. For example, the concentration of a supplied environmental component is highest in the second layer and lowest in the fourth layer. The concentration of a supplied nutrient is highest in the fourth layer and lowest in the second layer. Therefore, it is possible to improve work efficiency in selection of culture conditions, and it is thus possible to increase the possibility of acquisition of a microorganism that is difficult to be cultured.

It is possible to culture a microorganism only by circulating an environmental component-containing liquid or an environmental component-containing gas in the first layer and circulating a nutrient-containing liquid or a nutrient-containing gas in the seventh layer, and it is thus possible to perform culture of the microorganism easily. Consequently, it is possible to increase the possibility of acquisition of a microorganism that is difficult to be cultured. It is possible to assemble the apparatus by only coupling the first-type frame bodies 1 and the second-type frame bodies 2 to each other, and it is thus possible to improve efficiency in the production of the apparatus.

In some aspects, it is possible to detach the first-type frame bodies 1 and the second-type frame bodies 2 easily by only releasing the coupling and possible to newly couple another first-type frame body 1 or second-type frame body 2 instead. That is, each layer is easily replaceable. Therefore, it is possible to change culture conditions easily and possible to improve work efficiency in selection of culture conditions, and it is thus possible to increase the possibility of acquisition of a microorganism that is difficult to be cultured. For example, the fifth layer and/or the seventh layer that is a nutrient supply portion can be replaced with the first-type frame body 1 or the second-type frame body 2 that is another nutrient supply portion, or can be replaced with the first-type frame body 1 or the second-type frame body 2 that is an environmental component supply portion. In addition, the first layer that is an environmental component supply portion can be replaced with the first-type frame body 1 or the second-type frame body 2 that is another environmental component supply portion or can be replaced with the first-type frame body 1 or the second-type frame body 2 that is a nutrient supply portion.

In some aspects, it is possible to increase the number of layers to increase the number of three-layer stack structure bodies each having the nutrient supply portion B and/or the environmental component supply portion C at both surfaces of the culture portion A. Then, culture conditions can be varied for each of these three-layer stack structure bodies. Therefore, it is possible to improve work efficiency in selection of culture conditions, and it is thus possible to increase the possibility of acquisition of a microorganism that is difficult to be cultured.

In some aspects, it is possible to change at least one of the type and the concentration of a nutrient-containing liquid or a nutrient-containing gas that is circulated in the fifth layer and/or the seventh layer. It is also possible to change at least one of the type and the concentration of an environmental component-containing liquid or an environmental component-containing gas that is circulated in the first layer. Therefore, it is possible to realize various culture conditions easily and possible to easily perform work of selection of culture conditions suitable for a microorganism.

In some aspects, it is possible to detect and monitor culture states of microorganisms in the second layer to the fourth layer and the sixth layer by a temperature sensor 41 and/or a pH sensor 42. Therefore, it is possible to determine culture states in the layers rapidly and appropriately.

On the basis of a result of monitoring, in some aspects it is possible to change at least one of the type and the concentration of a nutrient-containing liquid or a nutrient-containing gas that is circulated in the fifth layer and/or the seventh layer and change at least one of the type and the concentration of an environmental component-containing liquid or an environmental component-containing gas that is circulated in the first layer. Therefore, it is possible to realize culture conditions suitable for a microorganism easily even in the middle of culture. In some aspects, it is possible to activate culture by applying vibrations to microorganisms in the second layer to the fourth layer and the sixth layer by an ultrasonic wave oscillator 43. Therefore, it is possible to improve efficiency in culture.

In addition the exemplary embodiments described above, various other alternative configurations are contemplated. For example, the first-type frame body 1 and the second-type frame body 2 are not limited to have annular shapes and may have outer shapes such as a triangular shape, a quadrangular shape, other polygonal shapes, or an elliptical shape in plan view. Coupling between the first-type frame bodies 1 and coupling between the first-type frame body 1 and the second-type frame body 2 are not limited to be performed by using a screw mechanism that uses an internal thread and an external thread and may be performed by using, for example, a slide fitting mechanism, a recess-projection fitting mechanism or an external coupling member.

Figure 36:
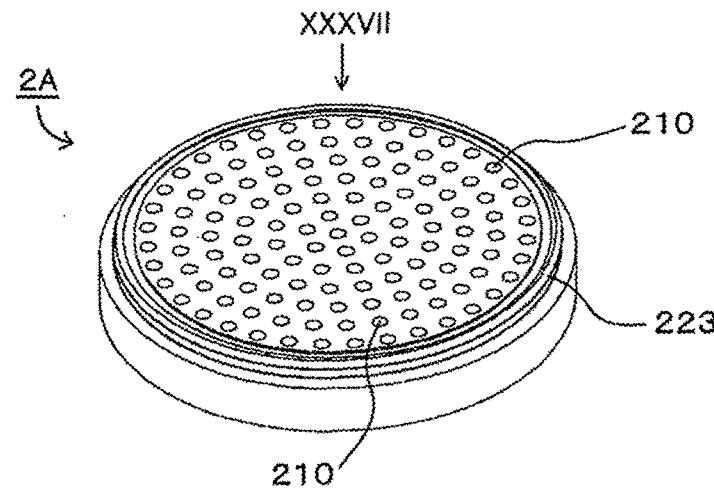
FIG. 36 is a perspective view illustrating a modification of the second-type frame body.
Figure 37:
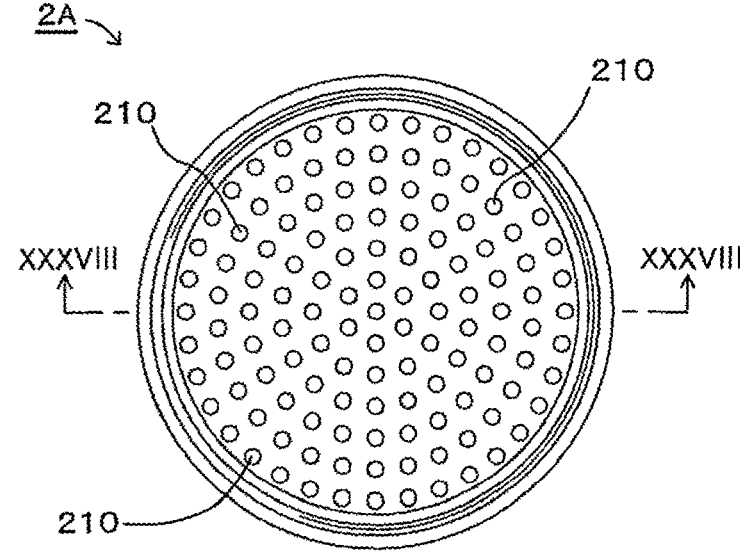
FIG. 37 is a view on arrow XXXVII in FIG. 36.
Figure 38:
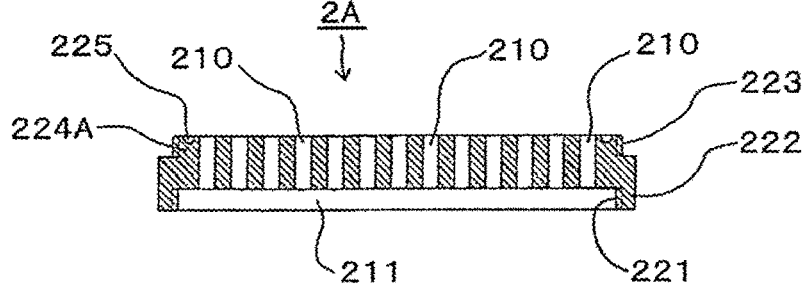
FIG. 38 is a sectional view along line XXXVIII-XXXVIII in FIG. 37.

In FIG. 36 to FIG. 38, a different second-type frame body 2A is illustrated. In the second-type frame body 2A, the second internal space 21 is constituted by a large number of through holes 210. FIG. 36 is a perspective view of the second-type frame body 2A. FIG. 37 is a view on arrow XXXVII in FIG. 36. FIG. 38 is a sectional view along line XXXVIII-XXXVIII in FIG. 37. The second-type frame body 2A includes, at a lower portion thereof, the annular external fitting portion 222 having the internal thread 221 and includes, at an upper portion thereof, an internal fitting portion 224A having the external thread 223. The second internal space 21 includes the internal space 211 surrounded by the external fitting portion 222 and an internal space other than the internal space 211, comprising the large number of through holes 210. In the second-type frame body 2A, a microorganism-containing medium is packed in all of the through holes 210.

Figure 39:
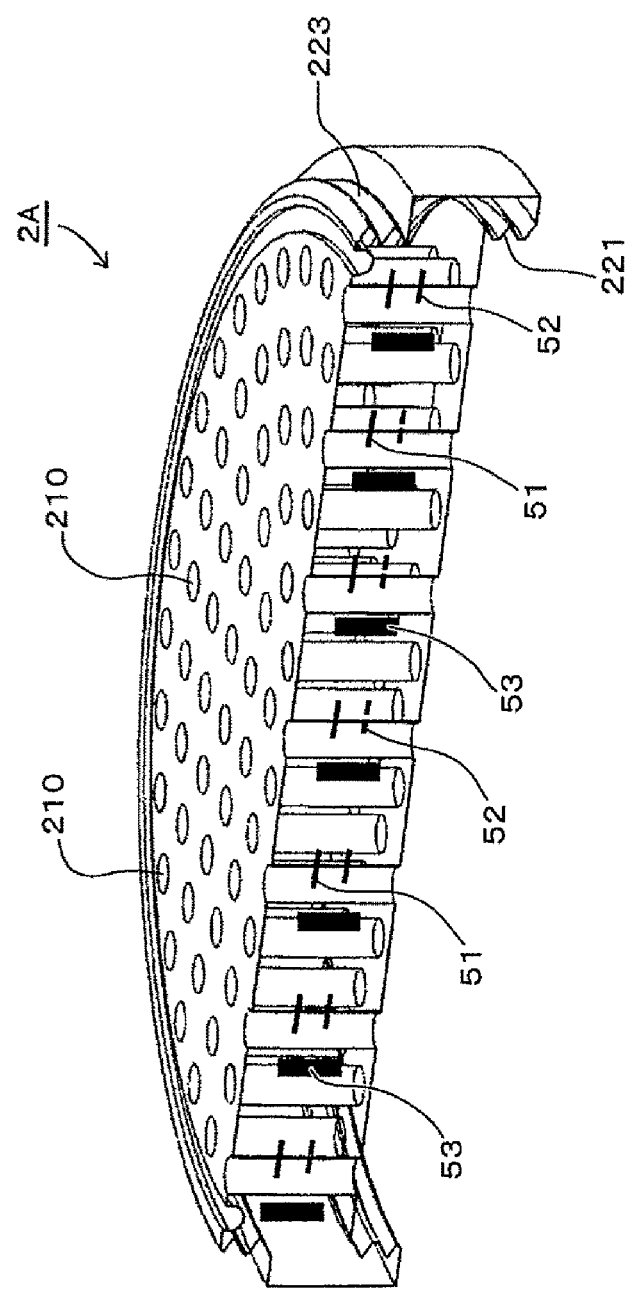
FIG. 39 is an enlarged sectional perspective view of the second-type frame body in FIG. 36.
Figure 40:
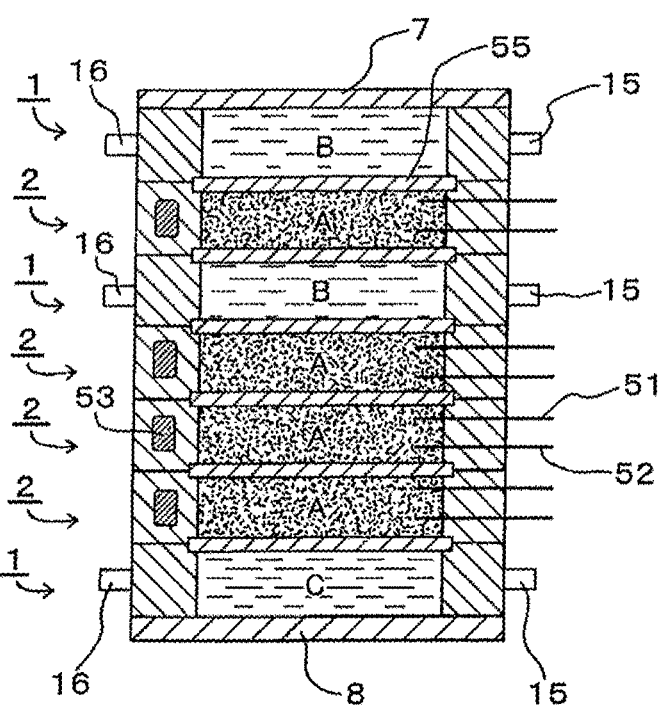
FIG. 40 is a schematic sectional view illustrating a microorganism culture apparatus used in an example.
Figure 41:
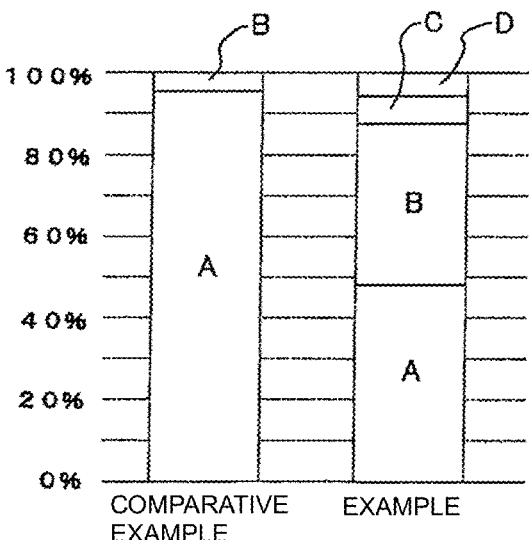
FIG. 41 shows results of examples.

As illustrated in FIG. 39, the second-type frame body 2A may be provided with the temperature sensor 41, the pH sensor 42, and the ultrasonic wave oscillator 43. These are provided in each of the through holes 210. The temperature sensor 41 and the pH sensor 42 are disposed in the inner portion of the second-type frame body 2A to detect the temperature and pH of the microorganism-containing medium packed in the through holes 210 and are connected to an external device (not illustrated). The external device is able to monitor the temperature and pH of the microorganism-containing medium via both of the sensors 41 and 42. The ultrasonic wave oscillator 43 is disposed in the inner portion of the second-type frame body 2A to be able to apply vibrations to the microorganism-containing medium packed in the through holes 210.

The internal space 212 (FIG. 18) of the second-type frame body 2 constituting the culture portion A may be a space that is optionally partitioned in the lateral direction or a space that is optionally partitioned in the up-down direction.

When the first-type frame body 1 is used as the culture portion A in a state in which the inflow passage 13 and the outflow passage 14 are closed, the first internal space 11 may be a space that is optionally partitioned in the lateral direction or a space that is optionally partitioned in the up-down direction.

A mechanism that opens and closes the inflow passage 13 and the outflow passage 14 is not limited to a mechanism using the plug 17 and may be a mechanism using an opening-closing cap, a mechanism using a check valve, or the like.

EXAMPLES

Example #1

A microorganism culture apparatus 100E configured by using the microorganism culture kit according to the fifth embodiment was tested in this experiment. As illustrated in FIG. 40, the first-type frame body 1, not the second-type frame body 2, was used as the fifth layer. The components of the culture apparatus 100E were configured as follows:

Nutrient supply portion (the seventh layer)
  Substrate A liquid
  R2A medium (Nihon Pharmaceutical Co., Ltd.) 0.32 g/100 mL
  Pure water 100 mL
Nutrient supply portion (the fifth layer)
  Substrate B liquid
    R2A medium (Nihon Pharmaceutical Co., Ltd.) 0.032 g/100 mL
      Pure water 100 mL
  Environmental component supply portion (the first layer)
    Soil extraction liquid
    Prepared in a ratio of pure water 15 g to soil 5 g.
  Culture portion (the second layer to the fourth layer and the sixth layer)
    Agar powder (Nacalai Tesque, Inc.) 1.5 g/100 mL
    Pure water 95 mL The above aqueous agar solution was treated in an autoclave (121° C./20 minutes), 5 mL of a soil-extraction dilute solution was added to the agar aqueous solution when the temperature of the agar aqueous solution reached about 60° C., and after stirred, the agar aqueous solution was packed in the internal space of a jacket as a culture portion. The soil-extraction dilute solution was prepared by stirring 15 mL of pure water after 5 g of soil was added to the pure water, and supernatant obtained after leaving the pure water for one hour was diluted by 10000 times through sequential dilution. A membrane filter VCWP (Merck Millipore Corporation; 0.1 μm) was disposed between portions.

Culturing was performed by circulating the substrate A liquid in the nutrient supply portion (the seventh layer), the substrate B liquid in the nutrient supply portion (the fifth layer), and the soil extraction liquid in the environmental-component supply portion (the first layer) continuously for one week.

After the culture, a colony generated in the culture portion was collected and subjected to a genetic analysis performed by Techno Suruga Laboratory Co., Ltd. Species were identified by performing a homology analysis on about 600 bases in the V1 to V4 regions of 16S rDNA and creating a simple molecular genealogical tree. The percentage of homology indicates the degree of matching between base sequences, and it was determined that a species was new when the percentage of homology was lower than 98%.

DNA extract achromopeptidase (FUJIFILM Wako Chemical Corporation)
PCR amplified PrimeSTAR HS DNA Polymerase (Takara Bio Inc.)
Cycle Sequence BigDye Terminator v3.1 Cycle Sequencing Kit (Applied Biosystems)
Base sequence determination ChromasPro 1.7 (Technelysium)
Database DB-BA 12.0 (Techno Suruga Laboratory Co., Ltd.)
  International base sequence database
  Search date: Mar. 15, 2018

Comparative Example #1

For comparison, a colony was generated by an agar-plate surface smear method and subjected to the same genetic analysis as Example #1 above.

FIG. 41 shows results of the genetic analysis. In FIG. 41, A indicates known species 100 to 98%, B indicates new species 98 to 94%, C indicates new genus 94 to 91%, and D indicates new order less than 91%. According to the example, about 40% of acquired microorganisms correspond to new species, and new microorganisms at a level of new order and new genus were also acquired. Accordingly, it was confirmed to be considerably effective for acquisition of microorganisms that are difficult to be cultured.

REFERENCE SIGNS LIST

1 first-type frame body
11 first internal space
12 first frame body
121 internal thread
123 external thread
13 inflow passage
14 outflow passage
15, 16 pipe
2 second-type frame body
21 second internal space
22 second-type frame body
221 internal thread
223 external thread
7 cap body,
8 base

The invention claimed is:

1. A microorganism culture kit comprising:
two frame bodies; and
a base, having a first-type fitting portion; and
a cap body, having a second-type fitting portion;
wherein the two frame bodies are each a first-type frame body or are the first-type frame body and a second-type frame body,
wherein the first-type frame body includes a first frame body surrounding a first internal space, the first frame body having a first-type fitting portion and a second-type fitting portion, and including an inflow passage for a fluid to flow into the first internal space and an outflow passage for the fluid to flow out from the first internal space, the inflow passage and the outflow passage being each provided to be openable and closable, wherein the second-type frame body includes a second frame body surrounding a second internal space, and having a first-type fitting portion and a second-type fitting portion, wherein the two frame bodies are stackable on each other;

wherein the first-type fitting portion and the second-type fitting portion are couplable; and wherein the cap body is configured to seal the first internal space and/or the second internal space of the frame bodies when they are stacked on each other, by covering the first internal space and/or the second internal space, except for the inflow passage and the outflow passage.

2. The microorganism culture kit according to claim 1, wherein the first-type frame body is configured, in a state in which the inflow passage and the outflow passage are open, to circulate a nutrient-containing gas, a nutrient-containing liquid, an environmental component-containing gas, or an environmental component-containing liquid in the first internal space and able, in a state in which the inflow passage and the outflow passage are closed, to hold a microorganism-containing medium, a nutrient-containing material, or an environmental component-containing material in the first internal space, and wherein the second-type frame body is configured to hold a microorganism-containing medium, a nutrient-containing material, or an environmental component-containing material in the second internal space.

3. The microorganism culture kit according to claim 1, wherein each of the two frame bodies has an annular shape and has an internal thread and an external thread, the two frame bodies being configured to be stacked on and coupled to each other as a result of the internal thread of one of the frame bodies being screwed with the external thread of the other of the frame bodies.

4. The microorganism culture kit according to claim 1, wherein the two frame bodies are each a first-type frame body.

5. The microorganism culture kit according to claim 1, wherein the first-type frame body includes a pipe extending outward from the inflow passage, wherein the pipe is configured to allow a fluid to be added to and flow into the inflow passage.

6. The microorganism culture kit according to claim 1, wherein the two frame bodies are each a second-type frame body.

7. The microorganism culture kit according to claim 1, wherein the first-type frame body includes a pipe extending outward from the outflow passage, wherein the pipe is configured to allow a fluid to flow into the outflow passage.

8. The microorganism culture kit according to claim 1, wherein the cap body is configured to close the first internal space and the second internal space of the frame bodies that are stacked on each other to cover the first internal space and the second internal space.

9. A method of culturing a microorganism, comprising:

providing a microorganism-containing medium; and placing the microorganism-containing medium in the microorganism culture kit of claim 1.

10. A method of culturing a microorganism, comprising:

providing a microorganism-containing medium; and placing the microorganism-containing medium in the first-type frame body or the second-type frame body of the microorganism culture kit of claim 2.

11. The method of culturing a microorganism of claim 10, wherein the microorganism-containing medium is placed in the first internal space of the first-type frame body.

12. The method of culturing a microorganism of claim 10, wherein the microorganism-containing medium is placed in the second internal space of the second-type frame body.

13. The microorganism culture kit according to claim 1, wherein the cap body comprises a circular plate body in plan view, comprising the second-type fitting portion at a lower portion thereof formed as an annular external fitting portion.

14. The microorganism culture kit according to claim 1, wherein the first-type frame body further comprises at least one of a temperature sensor, a pH sensor, or a gas concentration sensor.

15. The microorganism culture kit according to claim 1, wherein the first-type frame body further comprises an ultrasonic wave oscillator.

16. The microorganism culture kit according to claim 1, wherein the first-type frame body further comprises a temperature sensor, a pH sensor, and an ultrasonic wave oscillator.

*     *     *     *     *